United States Patent
Tang et al.

(10) Patent No.: US 9,212,977 B2
(45) Date of Patent: *Dec. 15, 2015

(54) CELL SEPARATION USING MICROCHANNEL HAVING PATTERNED POSTS

(75) Inventors: Zhongliang Tang, San Diego, CA (US); Pavel Tsinberg, Carlsbad, CA (US); Ram S. Bhatt, San Diego, CA (US)

(73) Assignee: BIOCEPT, INC., San Diego, CA (US)

( * ) Notice: Subject to any disclaimer, the term of this patent is extended or adjusted under 35 U.S.C. 154(b) by 564 days.

This patent is subject to a terminal disclaimer.

(21) Appl. No.: 13/525,225

(22) Filed: Jun. 15, 2012

(65) Prior Publication Data

US 2013/0121895 A1 May 16, 2013

Related U.S. Application Data

(63) Continuation of application No. 11/814,276, filed as application No. PCT/US2006/000383 on Jan. 5, 2006, now abandoned, which is a continuation-in-part of application No. 11/038,920, filed on Jan. 18, 2005, now Pat. No. 8,158,410.

(60) Provisional application No. 60/678,004, filed on May 4, 2005.

(51) Int. Cl.
*G01N 1/34* (2006.01)
*B01F 5/10* (2006.01)
(Continued)

(52) U.S. Cl.
CPC *G01N 1/34* (2013.01); *B01F 5/102* (2013.01); *B01F 13/0059* (2013.01);
(Continued)

(58) Field of Classification Search
CPC ........... G01N 1/34; G01N 1/40; G01N 1/405; G01N 33/54366; B01L 3/502753; B01L 3/502761
See application file for complete search history.

(56) References Cited

U.S. PATENT DOCUMENTS 4,151,075 A 4/1979 Othmer
4,436,827 A 3/1984 Tamagawa
(Continued)

FOREIGN PATENT DOCUMENTS

CN 1720438 1/2006
EP 1357178 10/2003
(Continued)

OTHER PUBLICATIONS

Office Action for U.S. Appl. No. 11/038,920, mailed Dec. 9, 2010.
(Continued)

*Primary Examiner* — Melanie Y Brown
(74) *Attorney, Agent, or Firm* — Cooley LLP

(57) ABSTRACT

A micro flow device (11, 71) for separating or isolating cells from a bodily fluid or other liquid sample uses a flow path where straight-line flow is interrupted by a pattern of transverse posts (23, 81). The posts are spaced across the width of an expanded collection chamber region (17, 75) in the flow path, extending between the upper and lower surfaces thereof; they have rectilinear surfaces, being curved in cross-sections, e.g. circular or tear-drop shaped, and are randomly arranged so as to disrupt streamlined flow. The device is oriented so that its lower surface is aligned at about 45° to the horizontal. Sequestering agents, such as Abs, which are attached to surfaces of the collection region via a hydrophilic coating, preferably a permeable hydrogel containing isocyanate moieties, are highly effective in capturing cells or other targeted biomolecules while the remainder of the liquid sample exits horizontally.

17 Claims, 7 Drawing Sheets

(51) Int. Cl.
  *B01F 13/00* (2006.01)
  *B01L 3/00* (2006.01)
  *G01N 1/40* (2006.01)
  *G01N 33/543* (2006.01)

(52) U.S. Cl.
  CPC ........... *B01L 3/502753* (2013.01); *G01N 1/40* (2013.01); *G01N 33/54366* (2013.01); *B01L 3/502761* (2013.01); *B01L 2300/0681* (2013.01); *B01L 2300/088* (2013.01); *B01L 2300/0816* (2013.01); *B01L 2400/0481* (2013.01); *B01L 2400/0487* (2013.01); *B01L 2400/0655* (2013.01); *B01L 2400/086* (2013.01); *G01N 1/405* (2013.01)

(56) References Cited

U.S. PATENT DOCUMENTS

| | | |
|---|---|---|
| 4,528,267 A | 7/1985 | Calenoff et al. |
| 4,675,286 A | 6/1987 | Calenoff |
| 5,147,607 A | 9/1992 | Mochida |
| 5,240,856 A | 8/1993 | Goffe et al. |
| 5,304,487 A | 4/1994 | Wilding et al. |
| 5,378,624 A | 1/1995 | Berenson et al. |
| 5,457,024 A | 10/1995 | Goldbard |
| 5,637,469 A | 6/1997 | Wilding et al. |
| 5,646,404 A | 7/1997 | Litzkow et al. |
| 5,672,481 A | 9/1997 | Minshall et al. |
| 5,695,989 A | 12/1997 | Kalamasz |
| 5,726,026 A | 3/1998 | Wilding et al. |
| 5,763,194 A | 6/1998 | Slowiaczek et al. |
| 5,858,653 A | 1/1999 | Duran |
| 5,906,724 A | 5/1999 | Sammons et al. |
| 6,008,040 A | 12/1999 | Datar |
| 6,027,623 A | 2/2000 | Ohkawa |
| 6,074,827 A | 6/2000 | Nelson et al. |
| 6,153,104 A | 11/2000 | Robertson |
| 6,156,270 A | 12/2000 | Buechler |
| 6,287,850 B1 | 9/2001 | Besemer et al. |
| 6,287,857 B1 | 9/2001 | O'Riordan et al. |
| 6,344,326 B1 | 2/2002 | Nelson et al. |
| 6,355,174 B1 | 3/2002 | Robertson |
| 6,368,871 B1 | 4/2002 | Christel et al. |
| 6,432,630 B1 | 8/2002 | Blankenstein |
| 6,433,179 B1 | 8/2002 | Wang et al. |
| 6,443,179 B1 | 9/2002 | Benavides et al. |
| 6,454,924 B2 | 9/2002 | Jedrzejewski et al. |
| 6,500,394 B1 | 12/2002 | Fulford |
| 6,569,324 B1 | 5/2003 | Moon et al. |
| 6,685,841 B2 | 2/2004 | Lopez et al. |
| 6,720,157 B2 | 4/2004 | Indermuhle et al. |
| 6,774,616 B2 | 8/2004 | Huhn et al. |
| 6,902,534 B2 | 6/2005 | Crawford et al. |
| 6,960,467 B2 | 11/2005 | Shieh et al. |
| 7,195,872 B2 | 3/2007 | Agrawal et al. |
| 7,217,520 B2 | 5/2007 | Tsinberg et al. |
| 7,695,956 B2 | 4/2010 | Tsinberg et al. |
| 8,158,410 B2 | 4/2012 | Tang et al. |
| 2002/0019062 A1 | 2/2002 | Lea et al. |
| 2002/0132316 A1 | 9/2002 | Wang |
| 2002/0143272 A1* | 10/2002 | Crawford et al. .............. 600/573 |
| 2002/0166760 A1* | 11/2002 | Prentiss et al. ................ 204/155 |
| 2003/0138969 A1 | 7/2003 | Jakobsen et al. |
| 2003/0153028 A1 | 8/2003 | Refseth et al. |
| 2003/0182900 A1 | 10/2003 | Bowden et al. |
| 2004/0038316 A1 | 2/2004 | Kaiser et al. |
| 2004/0142463 A1 | 7/2004 | Walker et al. |
| 2004/0177397 A1 | 9/2004 | Wangh |
| 2004/0197832 A1 | 10/2004 | Amiel et al. |
| 2004/0228770 A1 | 11/2004 | Gandhi et al. |
| 2004/0229349 A1 | 11/2004 | Daridon |
| 2004/0231851 A1 | 11/2004 | Silvers |
| 2005/0042766 A1 | 2/2005 | Ohman et al. |
| 2005/0092662 A1 | 5/2005 | Gilbert et al. |
| 2005/0112650 A1 | 5/2005 | Chang et al. |
| 2005/0192759 A1 | 9/2005 | Miyake et al. |
| 2005/0266433 A1 | 12/2005 | Kapur et al. |
| 2005/0282293 A1 | 12/2005 | Cosman et al. |
| 2006/0000772 A1 | 1/2006 | Sano et al. |
| 2006/0011480 A1 | 1/2006 | Sano et al. |
| 2006/0035386 A1 | 2/2006 | Hattori et al. |
| 2006/0121624 A1 | 6/2006 | Huang et al. |
| 2006/0134599 A1 | 6/2006 | Toner et al. |
| 2006/0141045 A1 | 6/2006 | Bhatt et al. |
| 2006/0160243 A1 | 7/2006 | Tang et al. |
| 2006/0223178 A1 | 10/2006 | Barber et al. |
| 2006/0252087 A1 | 11/2006 | Tang et al. |
| 2007/0026381 A1 | 2/2007 | Huang et al. |
| 2007/0026413 A1 | 2/2007 | Toner et al. |
| 2007/0026414 A1 | 2/2007 | Fuchs et al. |
| 2007/0026415 A1 | 2/2007 | Fuchs et al. |
| 2007/0026416 A1 | 2/2007 | Fuchs |
| 2007/0026417 A1 | 2/2007 | Fuchs et al. |
| 2007/0026418 A1 | 2/2007 | Fuchs et al. |
| 2007/0026419 A1 | 2/2007 | Fuchs et al. |
| 2007/0026469 A1 | 2/2007 | Fuchs et al. |
| 2007/0059680 A1 | 3/2007 | Kapur et al. |
| 2007/0059683 A1 | 3/2007 | Barber et al. |
| 2007/0059716 A1 | 3/2007 | Balis et al. |
| 2007/0059718 A1 | 3/2007 | Toner et al. |
| 2007/0059719 A1 | 3/2007 | Grisham et al. |
| 2007/0059774 A1 | 3/2007 | Grisham et al. |
| 2007/0059781 A1 | 3/2007 | Kapur et al. |
| 2007/0099207 A1 | 5/2007 | Fuchs et al. |
| 2007/0161051 A1 | 7/2007 | Tsinberg et al. |
| 2007/0172903 A1 | 7/2007 | Toner et al. |
| 2007/0196820 A1 | 8/2007 | Kapur et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2009/0136982 A1 | 5/2009 | Tang et al. |
| 2010/0167337 A1 | 7/2010 | Tsinberg et al. |
| 2010/0255479 A1 | 10/2010 | Mikolajczyk et al. |
| 2012/0100538 A1 | 4/2012 | Mikolajczyk et al. |
| 2012/0258475 A1 | 10/2012 | Tang et al. |

FOREIGN PATENT DOCUMENTS

| | | |
|---|---|---|
| EP | 1371419 | 12/2003 |
| EP | 1413346 | 4/2004 |
| JP | H09-094086 | 4/1997 |
| JP | H10-506991 | 7/1998 |
| JP | 2001-515216 | 9/2001 |
| JP | 2002-524755 | 8/2002 |
| JP | 2003-530566 | 10/2003 |
| JP | 2004-147555 | 5/2004 |
| JP | 2005-521425 | 7/2005 |
| JP | 2008-526251 | 7/2008 |
| JP | 2009-523429 | 6/2009 |
| WO | WO 96/10747 | 4/1996 |
| WO | WO 99/09042 | 2/1999 |
| WO | WO 00/15321 | 3/2000 |
| WO | WO 01/77641 | 10/2001 |
| WO | WO 02/23180 | 3/2002 |
| WO | WO 02/081662 | 10/2002 |
| WO | WO 03/085379 | 10/2003 |
| WO | WO 03/106031 | 12/2003 |
| WO | WO 2004/029221 | 4/2004 |
| WO | WO 2004/040318 | 5/2004 |
| WO | WO 2004/051231 | 6/2004 |
| WO | WO 2004/082796 | 9/2004 |
| WO | WO 2005/084374 | 9/2005 |
| WO | WO 2005/084380 | 9/2005 |
| WO | WO 2006/052223 | 5/2006 |
| WO | WO 2006/078470 | 7/2006 |
| WO | WO 2006/108087 | 10/2006 |
| WO | WO 2006/108101 | 10/2006 |
| WO | WO 2007/035414 | 3/2007 |
| WO | WO 2007/035498 | 3/2007 |
| WO | WO 2007/035585 | 3/2007 |
| WO | WO 2007/035586 | 3/2007 |
| WO | WO 2007/079229 | 7/2007 |

(56) References Cited

FOREIGN PATENT DOCUMENTS

| WO | WO 2007/079250 | 7/2007 |
|---|---|---|
| WO | WO 2007/082302 | 7/2007 |
| WO | WO 2008/011486 | 1/2008 |

OTHER PUBLICATIONS

Office Action for U.S. Appl. No. 11/038,920, mailed Apr. 9, 2010.
Office Action for U.S. Appl. No. 11/038,920, mailed Oct. 23, 2008.
Office Action for U.S. Appl. No. 11/038,920, mailed Jul. 20, 2009.
Office Action for U.S. Appl. No. 11/038,920, mailed Jul. 14, 2011.
Office Action for U.S. Appl. No. 11/458,668, mailed Oct. 7, 2011.
Office Action for U.S. Appl. No. 11/458,668, mailed Apr. 17, 2009.
Office Action for U.S. Appl. No. 11/458,668, mailed Aug. 28, 2008.
Office Action for U.S. Appl. No. 11/458,668, mailed May 13, 2008.
International Search Report and Written Opinion for International Application No. PCT/US2007/073817, mailed Jul. 14, 2008.
International Preliminary Report on Patentability for International Application No. PCT/US2007/073817, mailed Jan. 20, 2009.
International Preliminary Report on Patentability for International Application No. PCT/US2006/000383, mailed Jul. 24, 2007.
International Search Report and Written Opinion for International Application No. PCT/US2006/000383, mailed Jul. 10, 2006.
Office Action for U.S. Appl. No. 11/814,276, mailed May 17, 2011.
Office Action for U.S. Appl. No. 11/814,276, mailed Sep. 9, 2010.
Office Action for U.S. Appl. No. 13/441,703, mailed Feb. 27, 2013.
Office Action for U.S. Appl. No. 13/441,703, mailed Sep. 12, 2013.
Office Action for U.S. Appl. No. 13/441,703, mailed Aug. 6, 2012.
Office Action for U.S. Appl. No. 11/331,988, mailed Aug. 25, 2009.
Office Action for U.S. Appl. No. 11/331,988, mailed Apr. 30, 2008.
Office Action for U.S. Appl. No. 11/331,988, mailed Oct. 4, 2007.
Office Action for U.S. Appl. No. 11/331,988, mailed Oct. 16, 2008.
International Search Report and Written Opinion for International Application No. PCT/US2007/060518, mailed Nov. 13, 2007.
International Search Report for International Application No. PCT/JP2000/006350, mailed Oct. 24, 2000.
Bianchi, D. W., "Prenatal diagnosis by analysis of fetal cells in maternal blood," J. Pediatrics, Dec. 1995, 127(6):847-856.
Chou, C.-F. et al., "Sorting by diffusion: an asymmetric obstacle course for continuous molecular separation," PNAS, Nov. 23, 1999, 96(24):13762-13765.
Conradie, E. H. et al., "SU-8 thick photoresist processing as a functional material for MEMS applications," Journal of Micromechancis and Microengineering, 2002, 12:368-374.
Cuatrecasas, P., "Protein purification by affinity chromatography. Derivatizations of agarose and polyacrylamide beads," The Journal of Biological Chemistry, Jun. 1970, 245(12):3059-3065.
Gomez, S. M. et al., "Capture of rare cells in suspension with antibody-coated polystyrene beads," Biotechnology Progress, 1999, 15(2):238-244.
Guerin, L. J. et al., "Simple and low cost fabrication of embedded microchannels by using a new thick-film photoplastic," International Conference on Solid State Sensors and Actuators, Transducers '97, Chicago, Jun. 16-19, 1997, 2:1419-1422.
L'Hostis, E. et al., "Microreactor and electrochemical detectors fabricated using Si and EPON SU-8," Sensors and Actuators B, 2000, 64(1-3):156-162.
Kawata, M. et al., "Transcriptional control of HLA-A,B,C antigen in human placental cytotrophoblast isolated using trophoblast- and HLA-specific monoclonal antibodies and the fluorescence-activated cell sorter," J. Exp. Med., Sep. 1984, 160:633-651.
Lorenz, H. et al., "SU-8: a low-cost negative resist for MEMS," Journal of Micromechancis and Microengineering, 1997, 7(121):121-124.
Lorenz, H. et al., "High-aspect-ratio, ultrathick, negative-tone near-UV photoresist and its applications for MEMS," Sensors and Actuators A, 1998, 64(1):33-39.
Simpson, J. L. et al., "Isolating fetal cells from maternal blood: Advances in prenatal diagnosis through molecular technology," JAMA, 1993, 270(19):2357-2361.
Takahashi, K. et al., "Non-destructive on-chip cell sorting system with real-time microscopic image processing," Journal of Nanobiotechnology, 2004, pp. 1-8, BioMed Central Ltd.
Van Der Heijden, G. W. et al., "Asymmetry in histone H3 variants and lysine methylation between paternal and maternal chromatin of the early mouse zygote," Mechanisms of Development, Sep. 2005, 122(9):1008-1022.
Whitesides, G. M., "The origins and the future of microfluidics," Nature, Jul. 2006, 442(27):368-373.

\* cited by examiner

Figure: Schematics of Coating of Channels with Antibodies

CELL SEPARATION USING MICROCHANNEL HAVING PATTERNED POSTS

CROSS-REFERENCE TO RELATED APPLICATIONS

This application is a Continuation of U.S. patent application Ser. No. 11/814,276 filed Nov. 25, 2008, now abandoned, entitled, "Cell Separation Using Microchannel Having Patterned Posts", which is a National Stage Application filed under 35 U.S.C. §371 for PCT Application No. PCT/US06/00383 filed Jan. 5, 2006, entitled, "Cell Separation Using Microchannel Having Patterned Posts", which is a Continuation-in-Part of Ser. No. 11/038,920 filed Jan. 18, 2005, now U.S. Pat. No. 8,158,410 entitled, "Cell Separation Using Microchannel Having Patterned Posts" and which also claims priority to Provisional Patent Application 60/678,004 filed May 4, 2005, entitled, "Recovery of Rare Cells using a Microchannel Apparatus with Patterned Posts", all of which are incorporated herein by reference in their entireties.

FIELD OF THE INVENTION

This invention relates to separation or isolation of target biomolecules from feed liquids and more particularly to methods and apparatus for separating desired target human cells from bodily fluids or the like.

BACKGROUND OF THE INVENTION

Effective isolation and collection of rare cells from a heterogeneous cell population remains of high interest, due to the increasing demand for isolated cell populations for use in disease diagnosis and treatment, e.g. gene therapy, as well as for basic scientific research. For example, pathologically changed cells, such as cancerous cells, can be separated from a larger normal cell population, and the cleaned cell populations may then be transplanted back into the patient.

Cell separation is a rapidly growing area of biomedical and clinical development, and improved methods of separating a desired cell subset from a complex population will permit a broader study and use of cells that have relatively uniform and defined characteristics. Cell separation is also widely used in research, e.g. to determine the effect of a drug or treatment on a targeted cell population, to investigate biological pathways, to isolate and study transformed or otherwise modified cell populations; etc. Present clinical uses include, for example, the isolation of hematopoietic stem cells for reconstitution of blood cells, particularly in combination with ablative chemo- and radiation therapy.

Published U.S. Patent Application No. 2004/038315 attaches releasable linkers to the interior luminal surfaces of capillary tubing, with the desired bound cells subsequently being released via a cleavage reagent and recovered. U.S. Published Patent Application No. 2002/132316 uses microchannel devices to separate cell populations through the use of a moving optical gradient field. U.S. Pat. No. 6,074,827 discloses the use of microfluidic devices that are constructed to have "enrichment channels" wherein electrophoresis is used to separate and identify particular nucleic acids from samples. Also mentioned is the optional use of antibodies or other binding fragments to retain a desired target biomaterial. U.S. Pat. No. 6,432,630 discloses a microflow system for guiding the flow of a fluid containing bioparticles through channels where selective deflection is employed, and it indicates that such systems may be used to separate fetal cells from maternal blood samples.

U.S. Pat. No. 6,454,924 discloses microfluidic devices wherein analyte-containing liquids are caused to flow generally downward past sample surfaces disposed atop upstanding pillars on which capture agents are attached, with the side surfaces of such pillars having been rendered hydrophobic so as to facilitate flow in channels that they define.

K. Takahashi et al., *J. Nanobiotechnology*, 2, 5 (13 Jun. 2004) (6 pp) disclose on-chip cell sorting systems wherein multiple microfluidic inlet passageways lead to a central cell-sorting region fashioned in a PDMS plate (made in a master mold created in photoresist epoxy resin) that is bonded to a glass plate. Agar gel electrodes are provided in the PDMS plate which facilitate the separation of undesired cells by the application of electrostatic forces that direct these cells into a parallel, continuous waste stream of buffer, during their flow through a short, cell-sorting region of confluence. A pre-filter which uses posts to physically trap large dust particles is also shown. Published International Application WO 2004/029221 discloses a similarly constructed microfluidic device that can be used for cell separation, such as separating fetal RBCs from maternal blood by selective lysis of maternal RBCs. A sample that contains cells may be introduced into a microfluidic channel device which separates whole cells; it contains a plurality of cylindrical obstacles, with the surfaces of the obstacles having binding moieties, e.g., antibodies, suitably coupled thereto, which moieties will bind to cells in the sample. U.S. Pat. No. 5,637,469 discloses microfluidic devices having a plurality of channels of a depth of 100 microns or less wherein binding moieties, such as antibodies, are immobilized on surfaces to capture biomolecules of interest which can be analyzed in situ. U.S. Pat. No. 5,147,607 teaches the use of devices for carrying out immunoassays, such as sandwich assays, where antibodies are mobilized in microchannels. A recessed area can be provided in the microchannel that contains a group of protrusions which extend upward from the bottom surface of the channel and to which the antibodies are immobilized.

The foregoing, briefly described references provide evidence that there is continuing searching for improved separation methods for isolating cells or other biomaterials from bodily fluids or the like.

SUMMARY OF THE INVENTION

The invention provides a microflow apparatus for recovering rare cells or other target biomolecules from relatively small amounts of bodily fluids or the like which incorporates at least one specially constructed microchannel device. Such device is constructed using a substrate that is formed with a channel-like flow path which incorporates a plurality of transverse fixed posts in a collection region; these posts are integral with the substrate and extend between the upper and lower surfaces of the channel. The posts are arranged in a particular irregular array pattern to disrupt straight-line flow therethrough and importantly to break-up regular streamlined flow through the array, thereby assuring collisions with the posts and promoting swirling and eddies in a bodily fluid or other liquid that is being caused to flow along this flow path through the collection region. The posts vary in size, e.g. cross-sectional diameter. Sequestering agents which are selected to capture the desired target biomolecules and thereby collect them within the collection region of the microchannel are appropriately attached to the surfaces of the transverse posts and all other surfaces throughout the entire collection region. Preferably a supply well is provided at a location upstream of the microchannel leading to the collection region. It has been found that, by orienting the microflow apparatus so that it is inclined to the horizontal, more complete cell separation can be achieved as a result of force vectors created by gravity.

In one particular aspect, the invention provides a method for separating biomolecules, such as cells, from a sample of bodily fluid or other liquid, which method comprises causing such a sample containing target biomolecules to flow downstream along a flow path in a microflow device from an inlet to an outlet, which flow path comprises a microchannel arrangement that includes a collection region of expanded cross section, while orienting the device so that said flow path collection region is aligned at an angle of about 30° to about 60° to the horizontal, separating target biomolecules from the flowing sample by (a) interrupting straight-line flow of the liquid through said collection region, as a result of blocking such flow with a plurality of separator posts located in said region, which posts are integral with an upper or lower surface of said microchannel and extend therefrom to the opposite surface thereof, said posts extending transverse to said flow path and being located in an irregular pattern that extends laterally across said collection region and prevents straight-line flow and streamlined flow therethrough, and all surfaces of said collection region including said posts having sequestering agents carried thereupon, and (b) capturing target biomolecules found in the flowing liquid sample on surfaces in the collection region by binding the target molecules to the sequestering agents as a result of flow disruption by said irregular posts and force vectors that result from gravity, which vectors are aligned at an acute angle to said lower surface of said collection region, and discharging the remainder of the liquid sample through the outlet.

In another particular aspect, the invention provides a microflow apparatus for separating biomolecules, such as cells, from a sample of bodily fluid or other liquid, which apparatus includes a device that comprises a body having a flow path defined therein through which such a sample containing target biomolecules can be caused to flow, the body having inlet passageway to said flow path, an outlet passageway therefrom, and a microchannel arrangement extending between said inlet and outlet passageways, and a closure plate, said microchannel arrangement includes a collection region having upper and lower surfaces, one of which is provided by said closure plate, and a plurality of transverse separator posts, said posts being integral with one of said upper and lower surfaces of said collection region and extending laterally across said flow path to the other of said surfaces provided by said closure plate, said posts being located in an irregular pattern so as to interrupt straight-line flow and streamlined flow of liquid through said region, said surfaces of said collection region, including said posts, carrying sequestering agents that will bind with target biomolecules, and said inlet being aligned at an angle of between about 120° to about 150° to said flow path through said collection region, whereby a sample can be fed substantially vertically downward through said inlet while said body is aligned with said flow path at about an angle of 30° to 60° to the horizontal and whereby said irregular pattern of said posts and force vectors resultant from gravity cause effective capture of target biomolecules in said collection region, particularly upon the lower surface thereof.

In a further particular aspect, the invention provides a microflow apparatus for separating biomolecules, such as cells, from a sample of a bodily fluid or other liquid, which apparatus comprises a body having a flow path defined as a cavity in a flat surface thereof through which such a sample containing target biomolecules can be caused to flow, the flow path having inlet means, outlet means, and a microchannel arrangement extending between said inlet and outlet means, which microchannel arrangement includes a collection region with a plurality of transverse separator posts located in said region, and closure plate means having a flat surface that abuts said body flat surface and closes said flow path cavity, said posts being integral with a base surface of said collection region and projecting therefrom so as to extend to the surface of said closure plate means, said posts being arranged in an irregular pattern extending laterally across said flow path in said collection region so as to interrupt straight-line flow and streamlined flow of liquid through said region, and all said surfaces of said collection region including said posts being coated with a hydrophilic permeable hydrogel and carrying sequestering agents that will bind with target biomolecules, whereby disruption of streamlined flow throughout said collection region as a result of said irregular pattern of said posts creates effective capture of target biomolecules on said surfaces in said collection region.

DETAILED DESCRIPTION OF THE PREFERRED EMBODIMENTS

Figure 1:
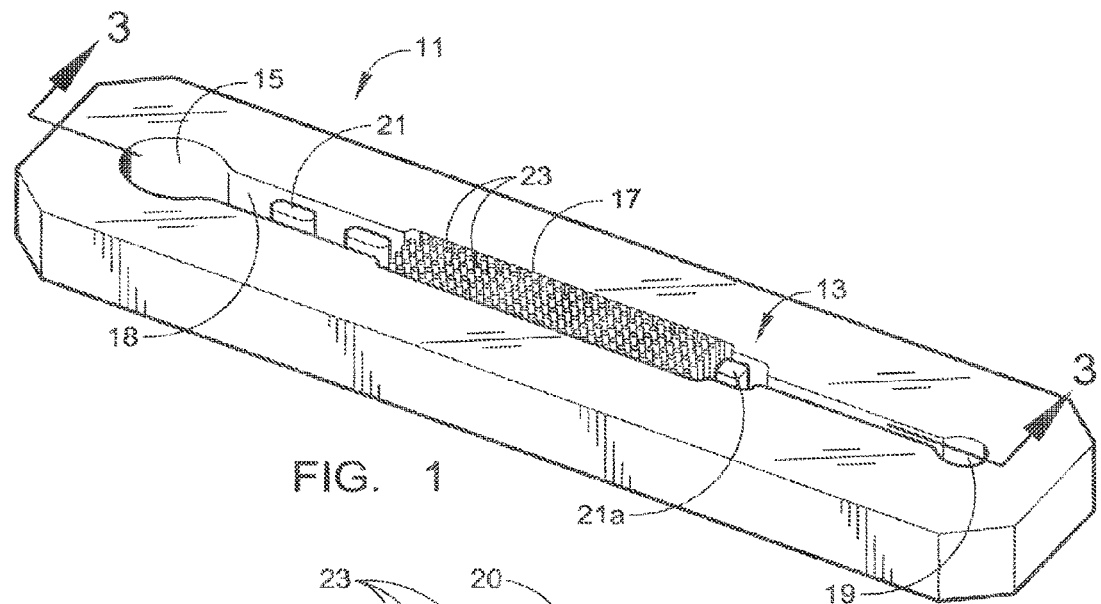
FIG. 1 is a perspective view of a substrate for a microflow device wherein there is fabricated a simplified post-containing collection region in a microchannel.

Basically an apparatus is provided which includes a device having a body or substrate 11 that has a flow path defined therein that includes at least one microchannel 13 having a collection region 17, which flow path is linked to a sample inlet 15 and a liquid outlet 19. As mentioned hereinafter, the flow path may include several microchannels, arranged in series, each of which has one such collection region. Alternatively, a microchannel may have more than one collection region, arranged in series, and there may also be more than one inlet and more than one outlet, all as well known in this art. Moreover it can be a part of an integrated microfluidic apparatus constructed on a chip, a disk or the like; in such an apparatus, substantially all of the MEMS (micro-electro-mechanical systems) or components needed to carry out cell recovery and/or diagnosis of biomolecules isolated from a sample may be incorporated as part of a single, compact, easily handled unit.

FIG. 1 is a perspective view of the body or substrate 11 which is formed with a flow path that includes a microchannel 13 to which sample liquid is to be supplied through an opening or well 15 that serves as an entrance or inlet and an opening 19 that serves as an outlet. The cross-section of the collection region 17 is greater than that of an inlet section 18 that leads thereinto from the inlet opening 15. The inlet section contains a pair of axially aligned divider/supports 21 just upstream of where it widens at the end of the region 18 to enter the collection region 17. These central dividers break the flow into two paths and serve to distribute the flow of liquid more evenly as it is delivered to the entrance end of the collection region 17. The collection region 17 contains a plurality of upstanding posts 23 that are aligned transverse to the liquid flow path and arranged in an irregular, generally random pattern across the entire width of the collection region portion of the flow channel. The pattern of the posts is such that there can be no straight-line flow through the collection region and that streamlined flow streams are disrupted, assuring there is good contact between the liquid being caused to flow along the flow path and the surfaces of the posts. The posts are integral with the flat base 22 of the collection region 17 and extend perpendicular thereto, presenting surfaces that are vertical relative to a horizontal path of liquid being caused to flow through the flow channel of the substrate 11. Preferably they extend to and are affixed at their free end surfaces as by bonding to the surface of a facing flat closure plate 27 which is parallel to the base surface 22 and which closes the flow channel, as is described in detail hereinafter. Inlet and outlet holes 24a and 24b may be drilled through such a closure plate, but they are preferably formed in the substrate 11. Another flow divider/support 21a is located at the exit from the collection region.

As is well known in this art, a substrate may be knitted with a flow path that includes a pair of parallel microchannels, each of which has a collection region. Such could be used in a series flow arrangement, or they could be used in parallel flow operation. Flow may be achieved by pumping, e.g. using a syringe pump or the like, or by vacuum that would draw liquid through from a reservoir at an inlet well provided by a large diameter inlet hole 24a. Preferably such a well is included which has a capacity to hold about 50 pi to about 500 μl of liquid sample.

The design of the flow channels is such that, at flow rates through the device within a reasonable range, e.g. injection of maternal blood using a standard Harvard Apparatus infusion syringe pump to create a flow in the collection region at a rate of about 0.05 to 5 min per second, there is substantial disruption of streamlined flow through the region without creating turbulence; this results from the random arrangement of posts of different sizes and the relative spacing of the posts throughout the collection region. Relatively smooth, non-streamlined flow without dead spots is achieved at a preferred average liquid flow rate of between about 0.1 to 2 mm/sec, and more preferably the average flow rate is maintained between about 0.2 and 1 mm/sec and is achieved by suction from an inlet well of defined size.

Figure 3:
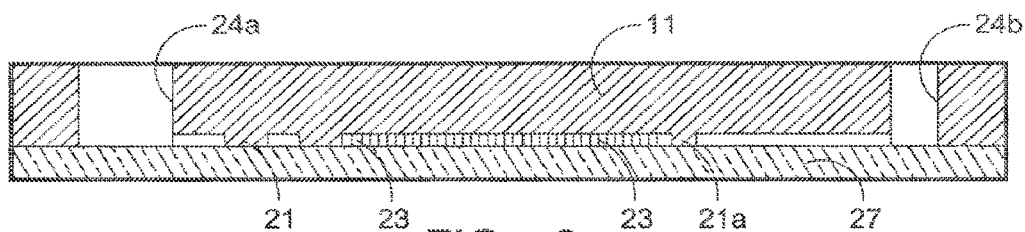
FIG. 3 is a front cross-sectional view of the substrate of FIG. 1 taken along the line 3-3 with a cover plate attached to its bottom surface.

Generally the substrate 11 can be made from any suitable laboratory-acceptable material, such as silicon, fused silica, glass and polymeric materials. It may be desirable to use a material that is optically transparent, particularly when a diagnosis function is desired to be optionally employed. In its simplest embodiment, the substrate carrying the fabricated microchannel is sealed with a plate 27 having a flat surface that will abut the facing surface of the substrate 11 as depicted in FIG. 3. Such plate may be fabricated from the same material or may simply be a solid cover plate made of glass; however, an intermediate flow regulation plate 25 may be included as explained hereinafter. Suitable solid impermeable plastics which may be used include polydimethylsiloxane (PDMS), polymethylmethacrylate (PMMA), polycarbonate, polystyrene, polyethylene teraphthalate, as well as other polymeric resins well known for acceptable laboratory material usage. Such patterned substrates may be fabricated using any convenient method such as those selected from among conventional molding and casting techniques.

Substrates may be conveniently fabricated from polymeric materials using a master or negative mold structure, which can be created in a thick negative photoresist, using optical lithography, as well known in this art and described in the *J. Nanobiotechnology* article, the disclosure of which is incorporated herein by reference. For example, the construction layer can be formed from a mixture of commercially available, standard grade epoxy resin (EPON SU-8) photoresist and hardener (SU-8 2025), which may be spun onto silicon wafer substrates at 2000 rpm to provide, for example, a 40 or 50 μm thick film of such photoresist. The thickness determines the height of the flow path in the collection region. The film is subjected to pre-exposure baking for 3 minutes at 60° C. and then 7 minutes at 95° C. on a precisely level hot plate to assure even thickness throughout, and the resultant samples are cooled to room temperature. A Karl Suss Contact Mask Aligner is used to expose a film with the desired pattern for the flow path in the ultimate device. The film is then post-baked at 65° C. for 2 minutes and then at 95° C. for 5 minutes before it is developed in a commercial SU-8 developer for 5 minutes, with light stirring being applied during developing. This creates a negative pattern mold in the epoxy resin photoresist that is then used as a molding master for replication of patterned post substrates in PDMS or other suitable polymeric resin.

As one example, a PDMS composition is prepared from a mixture of a PDMS prepolymer and a curing agent (Sylgard 184 kit, Dow Corning) at a 10:1 ratio by weight. The mixture is subjected to vacuum to evacuate bubbles that may be formed during mixing, before being poured over the epoxy resin master mold, which is located in a cavity of desired depth to create a substrate of desired thickness. The master mold may be optionally pre-coated with a thin layer (~50 nm) of a suitable metal (e.g. gold) to improve the release of the PDMS replica after curing. Curing of PDMS substrate may be carried out at 80° C. for 90 minutes; however, by initially undercuring the PDMS, it may be possible to facilitate subsequent functionalization of the collection region including the post surfaces as discussed hereinafter.

Figure 2:
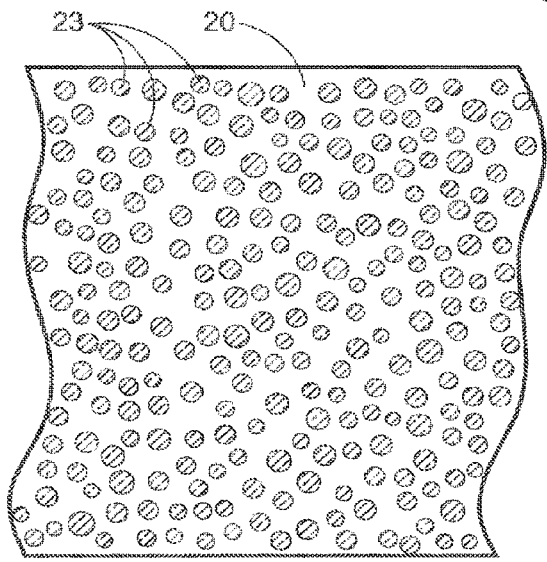
FIG. 2 is an enlarged fragmentary view showing a portion of the collection region of FIG. 1 where the patterned posts are located.

The layout and the dimensions of the microchannel 13 and of patterned posts 23 in the collection region 17 are determined by the mask used in exposure step of the fabrication of the master mold. The depth of the microchannel 13 is controlled by the thickness of the SU-8 layer of the master mold, which is determined by spin-coating conditions. FIG. 2 provides a top view of the microchannel 13 showing an enlargement of the posts 23 in the collection region 17 in a preferred generally random arrangement.

In alternative embodiments, holes 24 could be drilled into or otherwise created in the flat, unbroken surface of a released PDMS replica substrate or in the cover plate to provide for inlet and outlet connections. In the former instance, it could be mated with a simple microscope cover slip or other suitable flat plate, such as a thin flat piece of PDMS, that would provide an imperforate cover or base plate for the substrate. After subjecting the two components to plasma-cleaning for two minutes, the two cleaned surfaces are immediately placed in surface contact, without touching the facing surfaces, which then become sealed by surface reaction as well known in this art, forming a permanent seal and closing the microfluidic flow path.

Should it be desired to integrate on-chip flow management into such an apparatus, a separate SU-8 molding master incorporating cavities for flow regulation features, such as pneumatic valves and the like, may be similarly fabricated. A flow regulation plate or layer 25 produced from such a master mold would first be laminated to the microchannel substrate 11 (see FIGS. 4 and 5), and it would in turn be laminated to a flat closure plate 27. The employment of such flow-regulating components and other MEMS in a microflow apparatus is shown in U.S. Pat. Nos. 6,074,827 and 6,454,924, the disclosures of which are incorporated herein by reference. By carefully aligning such a flow regulation plate 25 with a microchannel carrying substrate 11 and then annealing overnight at 80° C., a composite structure is fabricated. Thereafter, cavities in the flow regulation plate 25 are closed by a flat plate or glass slide 27 using the same technique described earlier. As a further option, a second flow regulation plate might be laminated to the first plate 25, employing the same technique, should it be desired to incorporate still more sophisticated controls and optional processing.

Figure 5:
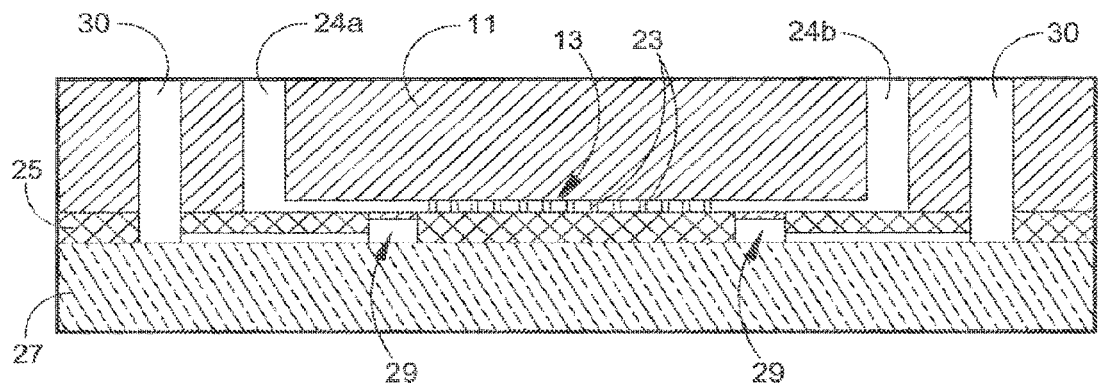
FIG. 5 is a cross-sectional view taken along line 5-5 of FIG. 4.
Figure 4:
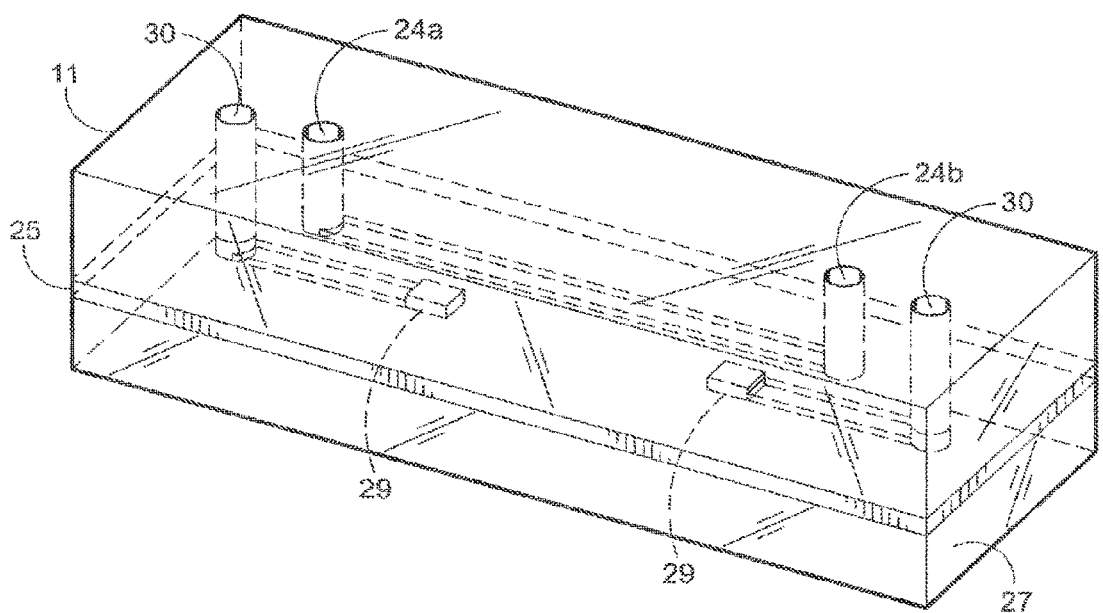
FIG. 4 is a schematic perspective view of an apparatus that incorporates two valves with a substrate as generally shown in FIG. 1 through the inclusion of an intermediate plate.

For example, on-chip flow regulation mechanisms could be provided in a multichannel system formed in a substrate 11 by disposing them in a flow regulation layer 25 that would be sealed to the substrate. A simple system is illustrated in FIGS. 4 and 5 where passageways 24a and 24b lead to the inlet and exit. Air supply to pneumatic valves 29 may be via drilled or otherwise suitably formed holes 30 that extend through the substrate 11 into the plate 25. The flow regulation plate 25 or the substrate 11 could optionally contain alternative supply passageways that could deliver liquid to the inlet 15 and also might include an alternative exit or removal passageway as well known in this art.

As mentioned, an arrangement wherein two series-connected collection regions are provided, lends itself to different methods of operation and use. For example, when a sample liquid is to be treated that potentially contains two different subpopulations of target biomolecules or cells of interest, one type of sequestering agent can be attached to the posts in one collection region or chamber, and a different type of sequestering agent can be attached to posts in a downstream collection chamber. Alternatively, in an instance where the target cells are extremely rare, it might be desirable to attach the same sequestering agents to the posts in both collection chambers so as to enhance the likelihood of being able to capture nearly 100% of the cells in the liquid sample.

Figure 6:
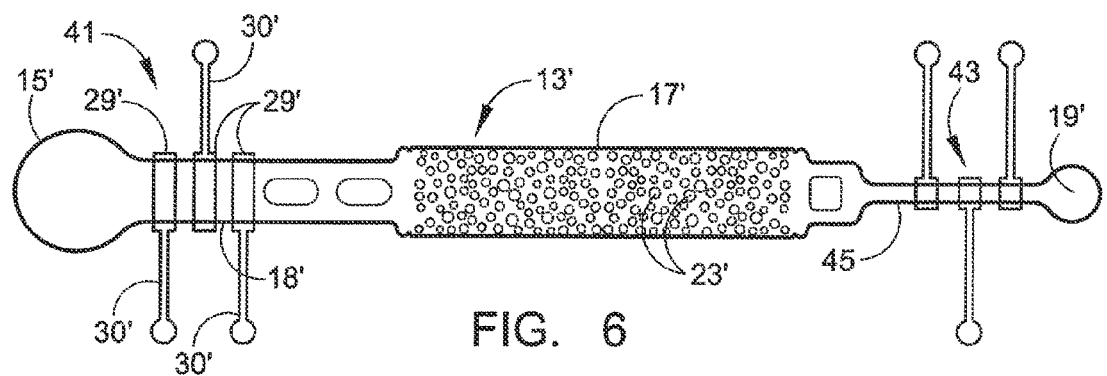
FIG. 6 is a schematic plan view showing a substrate of the type shown in FIG. 1, wherein pumps are fabricated as part of the microflow apparatus.
Figure 7:
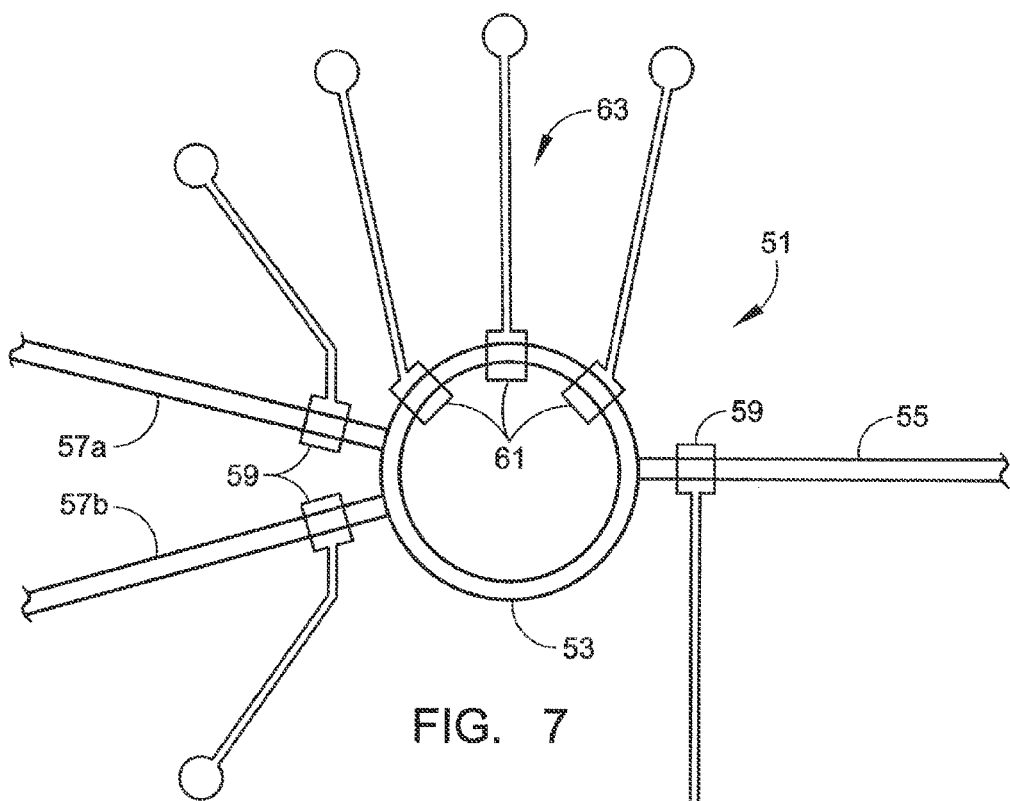
FIG. 7 is a schematic view of a portion of a substrate in which a micro-mixer is incorporated into the supply region.

From a constructional standpoint, some additional components that might optionally be incorporated into such an apparatus are illustrated in FIGS. 6 and 7. FIG. 6 shows a microchannel similar to that depicted in FIG. 1 in which peristaltic-type pump arrangements are incorporated into an inlet passageway region and an outlet passageway region flanking the collection chamber. Illustrated is a microchannel arrangement 13' that includes an inlet 15', a collection chamber 17' and an outlet 19' wherein an integrated pumping arrangement 41 is constructed by the incorporation of three specially designed membrane valves located in an entrance passageway 18' leading to the collection chamber. The schematic representation is of an arrangement similar to that shown in FIGS. 4 and 5 where the application of air or other high pressure gas to a passageway 30' leading to the pressure side of each valve membrane in a flow regulation layer or plate causes that membrane to expand, squeezing the liquid in the adjacent region of the microchannel with which it is associated. By programming a control unit so as to operate the three valves in sequence, from left to right, a wave movement is set up whereby the liquid in the entrance region 18' of the microchannel is pumped to the right and through the collection device 17'. If desired, a similar peristaltic-type pumping arrangement 43 is also incorporated into the exit passageway region 45 leading downstream from the collection chamber 17'.

As another potential alternative, a micromixing arrangement is illustrated in FIG. 7. A micromixer 51 is illustrated that includes a circular pathway 53 that leads to a supply passageway 55, which could be an entrance passageway leading to a collection chamber in a substrate such as earlier described. A pair of inlet channels 57a and 57b are provided to supply liquids to the circular pathway 53, and liquid flow through the pathways 55, 57a and 57b are controlled via pneumatic valves 59. Three additional pneumatic valves 61 are positioned in the passageway itself and constitute a peristaltic-type pump 63 of the type previously described. The arrangement provides an efficient way of micro-mixing two liquids in the substrate itself prior to delivery to a collection chamber or the like. For example, by filling the circular pathway 53 with some liquid from one inlet channel 57a and with some buffer from the inlet channel 57b, mixing can then be effected by operating the three valves 61 in sequence to pump the liquid around the ring provided in the circular pathway; thus, the liquid can be thoroughly mixed it before its discharge through a delivery passageway 55.

The polymeric surface of the patterned post region can be derivatized in various ways to enable the attachment onto all the surfaces of sequestering agents that are specific to the desired target cells or other biomolecules. For example, after plasma treatment and closure of the microchannel-carrying substrate, a 1 to 50 volume % solution of an amino-functional silane (e.g. a 10% solution of Dow Corning Z-6020), or a thio-functional silane, in ethanol may be injected into the microchannel to fill the region 17 between the openings 15 and 19, and the flooded microchannel 13 may then be left to incubate for 30 minutes at room temperature. Derivatization can be performed on a non-fully cured polymer, such as PDMS, before the closure of the microchannel region with the plate. In such case, as earlier mentioned, an alternative is to slightly undercure the PDMS substrate and then complete the curing after affixing the seal plate and treating with the substituted silane or other functionalizing reagent. For example, a final heating step of about 90 minutes at about 50 to 90° C. might be used to complete the curing after treating with the Z-6020. Alternatively one or two days at room temperature would also complete the curing. Such derivatization treatment may also be performed before the closure of the microchannel region because derivatization of the facing flat surface is no real consequence. The flow path is then purged with ethanol, and the microchannel is ready for attachment of biomolecule sequestering agents.

The term sequestering agent is used to refer to material capable of interacting in a specific fashion with a target biomolecule to physically sequester the target. These sequestering agents may include nucleic acids, such as DNA, RNA and PNA which bind to proteins; generally nonhybridization sequestering agents are employed comprising biological material, such as proteins, e.g. receptors, peptides, enzymes, enzyme inhibitors, enzyme substrates, immunoglobulins (particularly antibodies), antigens, lectins, modified proteins, modified peptides, double-stranded DNA, biogenic amines and complex carbohydrates. Synthetic molecules may also be used, e.g. drugs and synthetic ligands designed to have specific binding activity of this type. By "modified" proteins or polypeptides is meant those proteins or peptides having one or more amino acids within the molecule altered by the addition of new chemical moieties, by the removal of existing chemical moieties or by some combination of both removal and addition. This alteration may include both natural and synthetic modifications. Natural modifications may include, but are not limited to, phosphorylation, sulfation, glycosylation, nucleotide addition, and lipidation. Synthetic modifications may include, but are not limited to, chemical linkers to facilitate binding to the hydrogel, and microstructures, nanostructures, e.g. quantum dots, or other synthetic materials. In addition, modification may include the removal of existing functional moieties, e.g. hydroxyl, sulfhydryl or phenyl groups, or the removal or alteration of native side chains or the polypeptide amide backbone. Examples of complex carbohydrates include, but are not limited to, natural and synthetic linear and branched oligosaccharides, modified polysaccharides, e.g. glycolipids, peptidoglycans, glycosaminoglycans or acetylated species, as well as heterologous oligosaccharides, e.g. N-acetylglucosamine or sulfated species. Examples of naturally-occurring complex carbohydrates are chitin, hyaluronic acid, keratin sulfate, chondroitin sulfate, heparin, cellulose and carbohydrate moieties found on modified protein such as albumin and IgG. Combinations of two or more of such agents might be immobilized upon the posts, and such combinations might be added as a mixture of two entities or may be added serially.

Sequestering agents can be directly or indirectly immobilized upon the posts, and the posts may be pre-treated and/or coated to facilitate attachment. Indirect immobilization is clearly preferred and contemplates the employment of an intermediate agent or substance that is first linked to the post; moreover, it may be desirable to use coupling pairs to link the sequestering agent to the intermediate agent. For example, streptavidin, or an antibody directed against another species antibody, might be attached to the intermediate agent, which would thereafter couple to a biotinylated Ab or to an Ab of such other species. Such an arrangement permits a generic production of such microflow devices that might then be used to capture a variety of cells from different samples or to effect negative enrichment.

The use of Abs as sequestering agents may be preferred for cell separation, and their attachment is discussed in U.S. Pat. Nos. 5,646,404 and 4,675,286 and throughout the prior art. For example, procedures for non-covalent bonding are described in U.S. Pat. No. 4,528,267. Procedures for covalently bonding antibodies to solid supports are also described by Ichiro Chibata in IMMOBILIZED ENZYMES; Halstead Press: New York (1978) and in A. Cuatrecasas, *J. Bio. Chem.* 245:3059 (1970), the contents of both of which are hereby incorporated by reference. Kawata et al., *J. Exp. Med.*, 160:653 (1984) discloses a method for isolating placental cell populations by detecting target cells using cell-specific Abs, e.g. monoclonal antibodies against human trophoblasts (anti-Trop-1 and anti-Trop-2). U.S. Pat. No. 5,503,981 identifies three other monoclonal Abs which can be used for this purpose.

The antibody is preferably bound to the solid post surfaces indirectly, such as through the use of a surface layer or a coating of long linkers to which the Abs are then attached. For example, the surface can be first coated with a bifunctional or polyfunctional agent, such as a protein; the agent is then coupled with the antibody using a coupling agent, e.g., glutaraldehyde. The antibody can also be effectively bound by applying the antibody in aqueous solution to a surface that has been coated with a layer having free isocyanate or equivalent groups, such as a polyether isocyanate, or the antibody might be coupled to a hydroxylated material by cyanogen bromide. Particularly preferred is the use of a hydrophilic polyurethane-based hydrogel layer having free isocyanate groups, which is described hereinafter in connection with FIG. 9, or the use of a hydrophilic linker of substantial length, such as one of PEG, polyglycine, as described hereinafter in connection with FIG. 10.

The sequestering agents chosen are directed toward specific capture of the biomolecule of interest, which target biomolecules may be any of a wide variety of cells, as well as proteins, viruses, carbohydrates and the like; however, the invention is believed to exhibit particular efficiencies and have particular advantages in cell separation. Although the term "cell" is used throughout this application, it should be understood to include cell fragments and/or remnants that would likewise carry the surface ligands specific to the sequestering agents. Appropriate sequestering agents are selected, as known in this art, which would have high specific affinity in order to achieve such desired specificity to the target biomolecules. As mentioned above, such microflow devices may also be used for negative enrichment by targeting known contaminating cells.

When antibodies (Abs) are used, they are suitably attached, preferably through such intermediate agents, using any mechanisms well known in this art. For example, Abs may be treated with 2-aminothiolane to thiolate them, and the resulting thiolated Abs conjugated with posts that have been treated with PEG-maleimide; alternatively, the Abs may be directly covalently bonded to an appropriate hydrophilic coating having reactive isocyanate groups or thiocyanate groups.

With the antibodies or other sequestering agents in place throughout the patterned post collection region, the microchannel device is ready for use. A bodily fluid, such as a blood or urine sample, or some other pretreated liquid containing the target cell population, is caused to flow along a flow path through the collection region 17, as by being discharged carefully from a standard syringe pump into an inlet passageway 24a leading to the inlet 15 for such a microchannel device or drawn by a vacuum pump or the like therethrough from a sample reservoir provided by a relatively large diameter inlet passageway 24a which serves as well to hold the desired volume of sample for a test. The opening 24a may contain a fitting (not shown) for mating with tubing connected to such a syringe pump when such is used. The pump may be operated to effect a flow of about 0.5-10 µl/min. through the apparatus. Depending upon the bodily fluid, or other cell-containing liquid that is to be treated and/or analyzed, a pretreatment step may be used to reduce its volume and/or to deplete it of undesired biomolecules, as is known in this art.

To potentially increase the overall efficiency of a cell separation method, it may be desirable to collect the sample exiting the outlet 19 and cause it to flow through the microchannel device more than once; such repeat treatment may be particularly useful when the cells are particularly rare and thus are likely very few in number in the sample. However, because of the high efficiency of capture achieved by the apparatus, it is expected that such repeat flow will seldom be needed. Alternatively, two collection chambers linked in series might be used as earlier mentioned. Moreover, if somewhat larger volumes of bodily fluid samples are being processed, two or more microchannels could be used in parallel on a substrate.

Sequestering agents (e.g. Abs) are attached to the base, the facing surface, the posts and the sidewalls of the collection regions in the microchannels; however, such sidewall surfaces are not particularly effective in capturing cells as are the base, facing surface and the posts which disrupt the flow. It has been determined that flow of liquid containing cells or other biomolecules through even a confined lumen results in the cells being primarily present in the central flow stream region where flow shear is the least; as a result, capture upon sidewalls that carry sequestering agents is quite sparse in comparison to the capture upon surfaces in the immediate regions where the transverse posts have disrupted streamlined flow. In these regions, sequestering agents that can assume their native 3-dimensional configurations as a result of properly coupling are surprisingly effective.

Following the completion of flow of the liquid sample through the device, the targeted cells would, if present, have been captured within the collection region, and purging is first carried out with buffers so as to remove all of the extraneous biomaterial that had been part of the sample and that has not been strongly captured by the antibodies or other sequestering agents in the collection region. Such purging with effective buffers is expected to leave only the target cells attached in the collection region in the microchannel device, having removed all nonspecifically bound material.

Once purging with buffer has been completed, if the objective of the treatment method is cell collection alone, the captured cells are then suitably released. As mentioned hereinafter, in some instances, it may be desired that some analysis be carried out in situ. For example, the cells may be counted while attached, or they may be lysed and then subjected to PCR either in the collection chamber or downstream.

When release is to be effected, any method known in this art may be used, such as mechanical (e.g. high fluid flow), chemical (e.g. change in pH), or through the use of enzymatic cleavage agents or the like. For example, a reagent may be applied to cleave the sequestering agent or to cleave the bond between the agent and the cells in order to release the target cells from the collection region. For instance, trypsin or a specifically focused enzyme may be used to degrade the Abs and/or the cell surface antigens. Specific methods for both attaching Abs or the like and then effectively removing captured ligands are discussed in U.S. Pat. No. 5,378,624. For example, if the cells have been sequestered through the use of antibodies that are specific to surface characteristics of the rare cells, release may be effected by treating with a solution containing trypsin or another suitable protease, such as Proteinase K. Alternatively, a collagenase may be used to effect release from other sequestering agents, or a specifically cleavable linker may be used to attach the sequestering agent. During such cleavage, the outlet from the microchannel is connected to a reservoir or other collector, and the discharge stream carrying the released rare cells is collected for further analysis. The microchannel device may be fabricated with more than one exit passageway at the outlet and with valves for regulating which exit is open; such allows one exit passageway to be used for the waste discharge during the preliminary steps and then a different exit passageway to direct the target cell stream to a collection container.

It has been found that the placement and shape of the posts 23 in the patterned post collection region 17 can be engineered for optimal fluid dynamics and enhancement of capture of target cells through their specific surface characteristics. Very generally, in most instances, the preferred shape of the horizontal cross-section of the transverse fixed posts 23 avoids sharp angles which might promote nonspecific binding to the transverse surfaces of the posts. The posts 23 have rectilinear exterior surfaces and preferably have either a generally circular cross sectional shape or regular polygonal of 6 or more sides. Alternative shapes that might be used are tear-drop shape where the tip is at the downstream end and shallowly curved, or oval shape; however, should more impact be desired, a square shape might be used. The pattern of the posts should create a flow pattern in the liquid stream which enhances the capture of target cells by the sequestering agents attached to the surfaces of the posts, the base and the facing surface. To achieve this end, it has been found that the posts should be of different sizes and be arranged in a set random pattern. Surprisingly, a random pattern of posts 23 of different cross sectional sizes, e.g. circular cross section posts of at least about 3 or 4 different sizes, about 70 to about 130 microns in diameter, in a collection region about 100 microns high and about 2 to 4 mm wide, appears to promote a particularly effective capture of cells from the flow of a liquid sample, when the minimum separation spacing between posts is 50 to 70 μm and preferably about 60 μm.

It is particularly preferred that the cross sectional area of the posts, which all have sidewalls formed by parallel lines which are perpendicular to the base, is such that they occupy between and about 15 to 25% of the volume of the collection region. Preferably the post pattern will be such that they occupy about 20% of the volume of the collection region, leaving a void volume for liquid flow of about 80%. The particular random pattern of post locations shown in FIG. 2 appears to particularly enhance the tendency of the cells to be captured by sequestering agents in these regions where streamlined flow has been effectively disrupted. The posts 23 are substantially spaced apart from one another, e.g. by at least about 60 microns, and posts of different sizes are preferably located upstream and downstream of one another.

Smaller posts may create eddy regions downstream of larger posts, and as a result of the flow pattern that is generated, the surfaces in the vicinity, and particularly the bottom surface of the collection region, will show particular effectiveness in capturing target cells. As shown in FIG. 2, any straight line extending longitudinally of the flowpath at a location more than about 100 microns from a sidewall will intersect a plurality of posts. As previously mentioned, the posts are integral with the base 20 surface of the substrate and are preferably affixed at their opposite or free ends to the facing surface, i.e. either a flow-regulation plate 25 or a flat closure plate 27.

Figure 8:
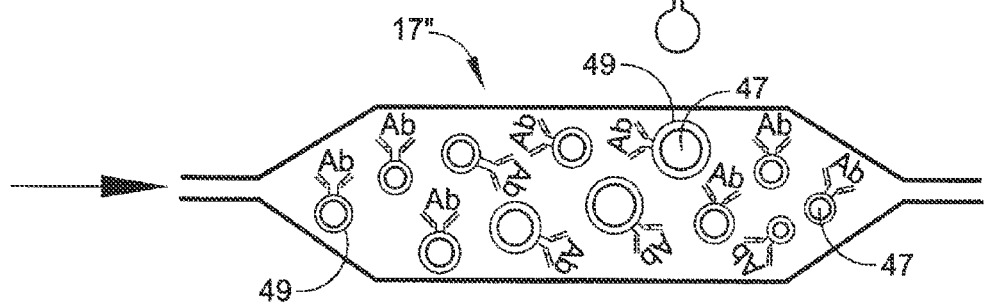
FIG. 8 is a schematic representation of antibodies attached throughout a collection region via the application of a hydrophilic coating.

As indicated before, the sequestering agents, such as antibodies, may be attached throughout the collection region in a manner such that they are able to perform more effectively by coating the surfaces with (a) a thin layer of a particular hydrophilic hydrogel substance or (b) hydrophilic linkers, such as PEG, polyglycine or the like of a molecular weight of at least about 1,000 daltons, preferably having a MW of about 2,000 to 100,000 daltons, and more preferably between about 3,000 and 50,000 daltons. Particularly preferred is the employment of (a), i.e. the hydrophilic permeable hydrogel coating which is an isocyanate-functional polymer containing PEG, PPG or a copolymer thereof that is polymerized by urethane bonds and that contains reactive isocyanate groups. A preferred hydrogel utilizes a three-leg PEG molecule of approximately 6,000 molecular weight that is created by the addition of ethylene oxide to glycerol. The resultant polyol is reacted with isophorone diisocyanate and trimethylol propane to prepare a prepolymer. A mixture of the prepolymer with appropriate buffer, solvent and other components for a particular application is crosslinked in situ upon surfaces of the collection region in a microflow device. Schematically shown in FIG. 8 is a representation of a collection region within a microchannel wherein there are a plurality of posts 61 of varying diameter that are randomly arranged to disrupt streamlined flow through the chamber, wherein each of the posts 61 and the facing flat surfaces carry an exterior coating 63. Sequestering agents 65 in the form of antibodies are depicted as being attached to the hydrophilic permeable hydrogel coatings on the posts; as a result, they retain their native three-dimensional confirmation, unaltered by attachment to the hydrogel which is primarily water and thus quite deformable.

Figure 9:
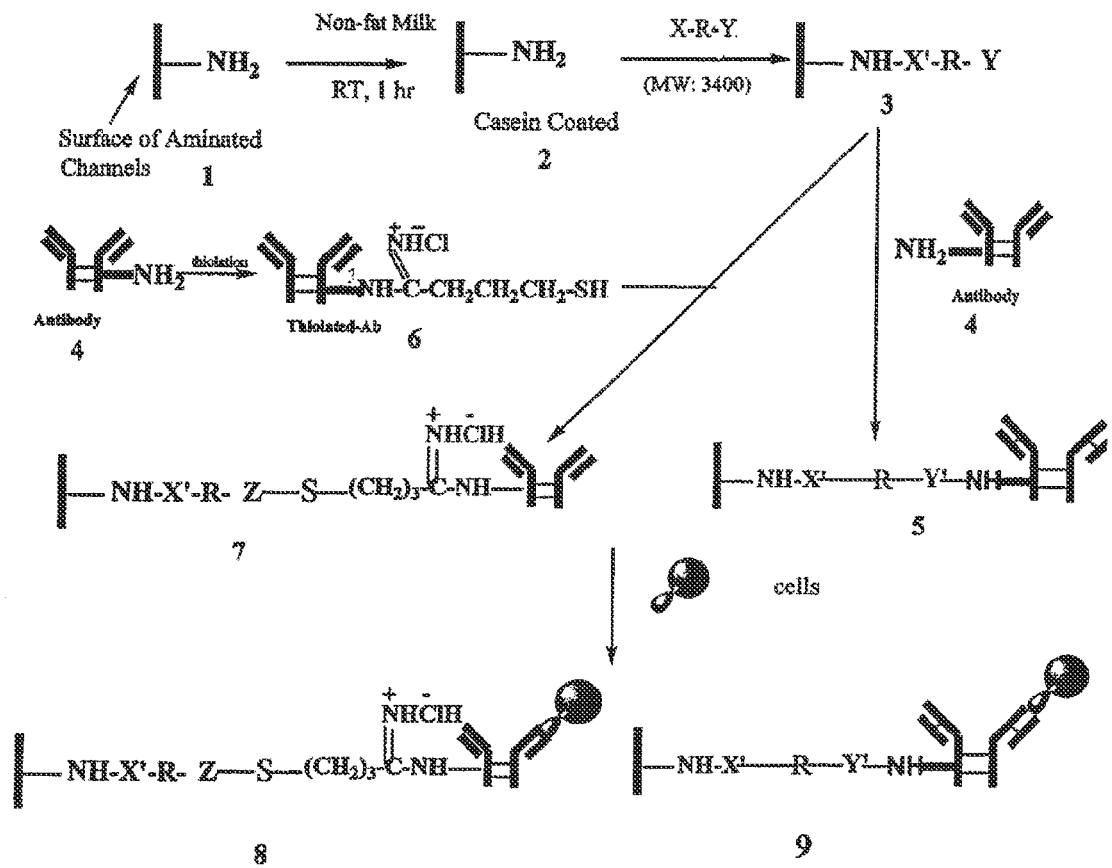
FIGS. 9 and 10 are schematic representations of chemistry that may be used to covalently attach sequestering agents, e.g., antibodies, throughout a collection region using a hydrophilic coating, along with depiction of subsequent capture of desired target cells.

FIG. 9 is provided as a schematic representation of chemistry that may be employed when a hydrophilic permeable hydrogel coating 49 of the preferred character is used, as in FIG. 8. Shown are representative sequences of attaching sequestering agents, i.e., antibodies, to all the surfaces throughout the collection region. Point 1 of FIG. 9 shows a surface following amino-derivatization by treatment with an aminosilane or the like. This step is followed by using non-fat milk to casein-coat the surfaces, see Point 2. Point 3 represents the coated surface after coating has been carried out. A prepolymer containing PEG of a molecular weight of about 3400 that is end-capped with toluenediisocyanate is dissolved in a water-miscible, organic solvent, preferably an aprotic solvent such as a mixture of NMP and $CH_3CN$. The polymer preferably contains tri- or higher functional polyols, e.g. PEGs and PPGs, and may contain trifunctional isocyanate. An aqueous solution is then prepared containing about 98.5 weight percent water, which solution is pumped through the microchannel so that the surfaces of the posts and the facing surfaces of the collection region become coated with this hydrophilic hydrogel coating, as a result of reaction of some of the end-capped isocyanate groups at the amine-derivatized surfaces. The end result is represented at Point 3 in FIG. 9, which is here a hydrogel which is created as a result of initial reaction with water and later formation of urea bonds.

Point 4 represents the addition of antibodies which will have surface amino groups. They can be attached directly to such hydrophilic permeable hydrogel coatings of the posts, as shown in Point 5, by covalent bonding of the Abs amines to either isocyanate or thiocyanate groups carried by the hydrophilic coating. Alternatively, the antibodies may first be thiolated as depicted at Point 6 of FIG. 9, and these thiolated antibodies then supplied in aqueous solution to the collection chambers, where they will in turn readily covalently bond to the isocyanate groups of the coated polymers, see Point 7.

As depicted at Points 8 and 9 in FIG. 9, when cells in a liquid sample that is being caused to flow through the collection chamber, as a result of the disrupted streamlined flow, come in contact with the posts and/or the facing surfaces, antigens on the cell surfaces specific to the antibodies become conjugated thereto, effectively capturing the cells.

Figure 10:
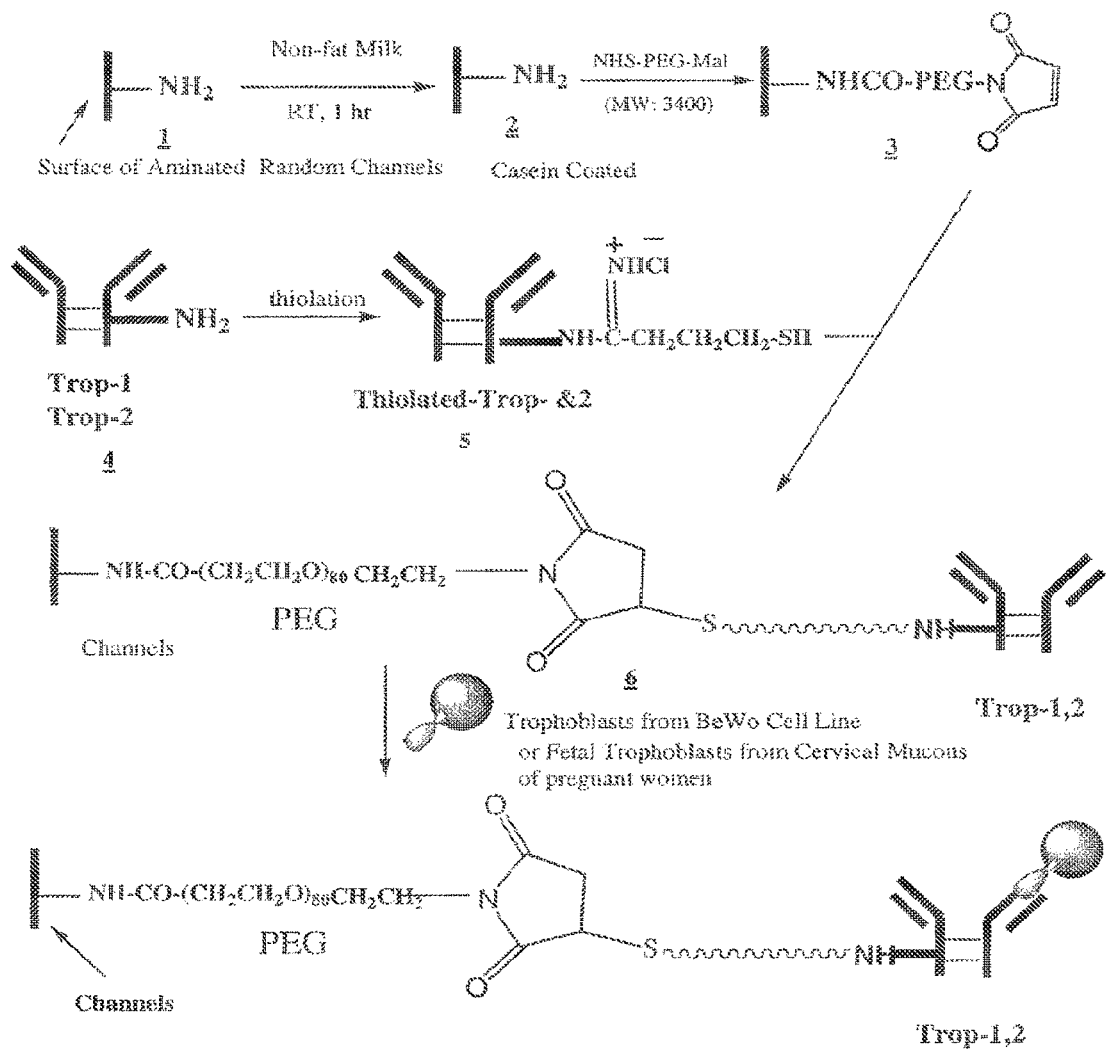

FIG. 10 is provided as a schematic representation of chemistry that may be employed when an elongated PEG or PPG linear polymer, instead of a hydrogel, is used to tether a sequestering agent, particularly an antibody, to the surfaces in a collection region. The linear polymer is selected so as to be of such length that the antibody will be able to assume its native three dimensional configuration in an aqueous environment where capture is being carried out. Point 1 of FIG. 10 shows the surface following amino-derivatization by treatment with an aminosilene or the like. This step is again followed by using non-fat milk solids to casein-coat the surfaces as described above. Following washing, all the surfaces are treated with a linear PEG or PPG having a molecular weight of at least about 2000, and preferably at least about 3000, which has a NHS moiety at one end and maleimidyl moiety at the opposite end. The N-hydroxy-succinimidyl ester moiety reacts readily with the amino groups on the surfaces to provide a coating at least about 1 micron thick. After suitable incubation, the microchannel is drained and washed with a suitable buffer, leaving the maleimido-PEG-coated surfaces as represented by point 3 of FIG. 10. Point 4 represents antibodies which are specific for trophoblasts and which inherently have surface amino groups. The antibodies are preferably thiolated using a suitable reagent, such as Traut's reagent, to reach the point depicted as point 5 in FIG. 10. The thiolated antibody is then conjugated with the maleimido-PEG-coated posts by introduction of the purified thiolated antibody into the microchannel in a buffered solution and allowing it to appropriately incubate. The microchannel is then washed with a suitable buffer, and the conjugated arrangement depicted as point 6 is obtained.

Point 7 of the schematic representation of FIG. 10 shows the capture of a trophoblast by an antibody that is tethered to a surface by the linear PEG coupling agent.

A more preferred, alternative construction of a microflow apparatus is illustrated in FIGS. 12-15. A microflow device 71 is shown which resembles that shown in FIGS. 1-3, but which is constructed to take advantage of gravity to create uniform flow, to improve contact between a liquid being treated and the surfaces interior of the device in the collection region, and to minimize attachment of the targeted cells in regions outside of the collection chamber, such as the inlet and outlet. In this respect, the apparatus is designed for use inclined at an angle of between about 30° and 60° to the horizontal, preferably at about 45°. Accordingly, the device includes a body or substrate 73 that includes a microchannel 75 that extends therethrough from an inlet passageway 77 to an outlet passageway 79, with a collection region 81 being located therebetween which includes an entrance region 83 and an exit region 85 as before. The collection region 81 is formed as a recess or a cavity in a flat surface 87 of the body, and the collection region itself has a flat base surface 89 that is substantially parallel to the surface 87 of the body. A plurality of posts 91, as described previously, extend from the base surface 89, perpendicular thereto, to the level of the body flat surface 87, together with flow dividers in the entrance and exit regions.

Figure 14:
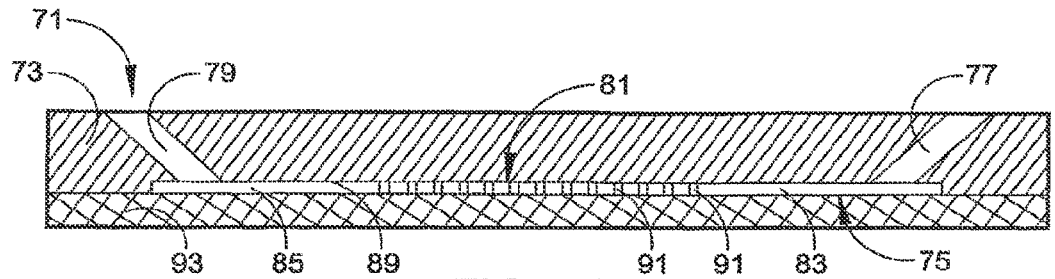
FIG. 14 is a front cross-sectional view, enlarged in size, taken along the line 14-14 of FIG. 12.
Figure 12:
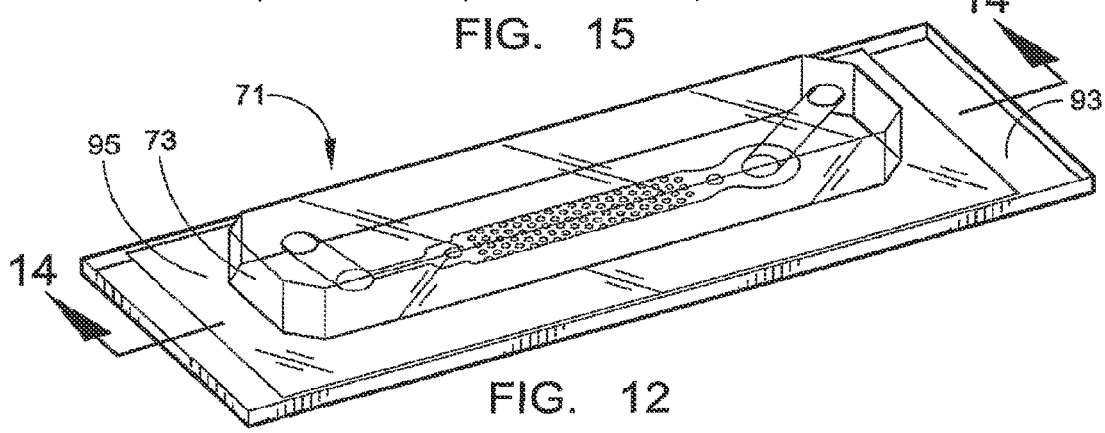
FIG. 12 is a perspective view of an alternative embodiment of a microflow apparatus wherein there is fabricated a post-containing collection region in a microchannel device designed for operation at an incline to the horizontal.
Figure 13:
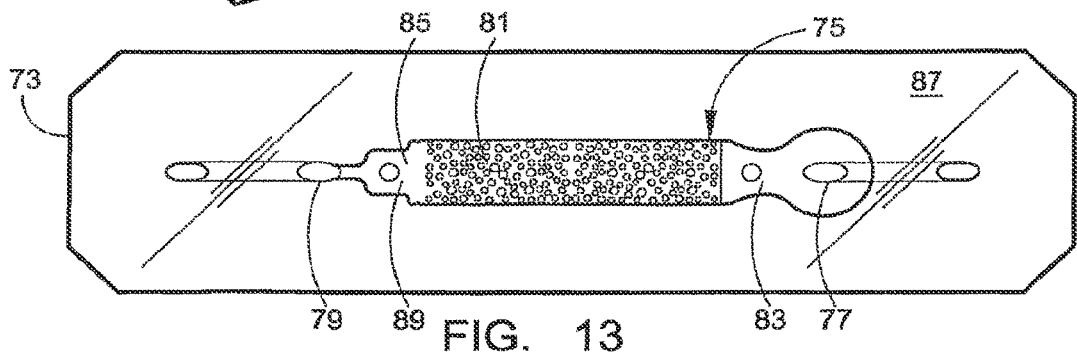
FIG. 13 is a bottom view of the body portion of the microflow device of FIG. 12.

Except for the orientation of the entrance and exit passageways 83, 85, the construction of the device 71 is essentially the same as described hereinbefore with regard to those devices depicted in FIGS. 1-5. As shown in FIGS. 12 and 14, the cavity which constitutes the microchannel 75 is closed with a flat solid plate 93 which is preferably of greater dimensions than the body 73 to facilitate handling of the completed apparatus during treatment and analysis of a liquid sample. The flat closure plate 93 may be made of glass or a suitable impermeable polymeric material as described hereinbefore. The plate 93 may be coated with a layer of the same polymeric material as that from which the body is cast, molded or otherwise suitably constructed. More preferably, a PDMS polymer is used, and if a standard glass slide about 25 mm by 75 mm is used, it may be coated with a layer or a thin film 95 of PDMS as indicated in FIG. 12. Attachment of the closure plate 93 could affix its flat surface to the end surfaces of the posts 91, as described hereinbefore, or they might simply be left to substantially abut.

Figure 15:
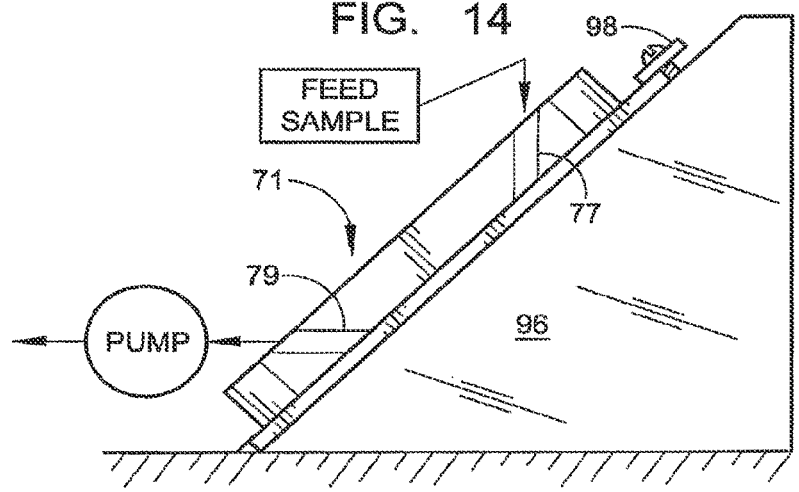
FIG. 15 is a schematic view showing the apparatus of FIG. 12 in use.

As best seen in FIG. 14, the inlet passageway 77 is aligned at an acute angle of 30° and 60° to the flat face surface of the microchannel which is parallel to the flow path therethrough; more preferably at an angle of between 40° and 50° and most preferably at about 45° thereto. This arrangement allows the feed sample to be fed vertically downward into the microflow apparatus 71, as schematically shown in FIG. 15, with the apparatus clamped along its upper edge to the oblique surface of a base 96 by a plate 98 so that the flow path therethrough is inclined to the vertical, e.g. at about 45°. Thus, the feed sample will fill the wide entrance region 83 to the collection region 81, and gravity assists in keeping the collection region, where the posts are located, full and promoting a desired slow and uniform flow therethrough. More importantly, because the liquid flow will be linearly through the chamber in a direction parallel to the upper and lower surfaces, and because the cells are heavier than the liquid aqueous buffer in which they are being transported, gravity will create a force vector on these cells different from the flow vector of the transporting liquid. As a result, in addition to the disruption of streamline flow that is created by the random pattern of posts of different sizes in the collection region, there is a further vector which causes the cells to escape from the flowing stream and adhere to a surface by attachment to a sequestering agent. This effect has been found to substantially improve cell collection even when there is a relatively slow flow through the collection region.

The inlet and outlet passageways 77, 79 are preferably located in the same vertical plane, and the orientation of the outlet passageway is preferably at about 90° thereto. Thus, when the apparatus 71 is clamped to the base 96 as shown in FIG. 15, with the inlet passageway 77 vertical, the outlet passageway 79 is horizontal. This allows the sample containing cells and other biomaterials that have not been bound by the Abs to exit horizontally, thus facilitating their removal and minimizing non-specific attachment within the flow channel and sedimentation in the outlet region.

FIG. 15 also depicts the presently preferred method of running a treatment wherein a sample is fed vertically into the inlet passageway to the microflow apparatus, and the outlet passageway 79 is connected via suitable tubing to the suction side of a syringe pump or the like which then facilitates the flow of sample through the apparatus at the desired flow rate. The flow rate is carefully controlled so that the liquid sample is withdrawn at a rate so that the average velocity of liquid flow in the collection region is between about 0.1 and about 1 mm/sec, preferably between about 0.2 and about 0.8 mm/sec and more preferably between about 0.25 and about 0.5 mm/sec, which has been found to maximize capture of the targeted cells as a result of the flow disruption of the posts and the force vectors resultant from gravity. Higher velocities are found to be less effective and may injure delicate cells that might be sought. Although the apparatus is illustrated in its simplest form, it should be understood that various valves and ancillary components, as known in these MEMS devices and as generally described hereinbefore, can be incorporated together with the microflow device 71.

Figure 11:
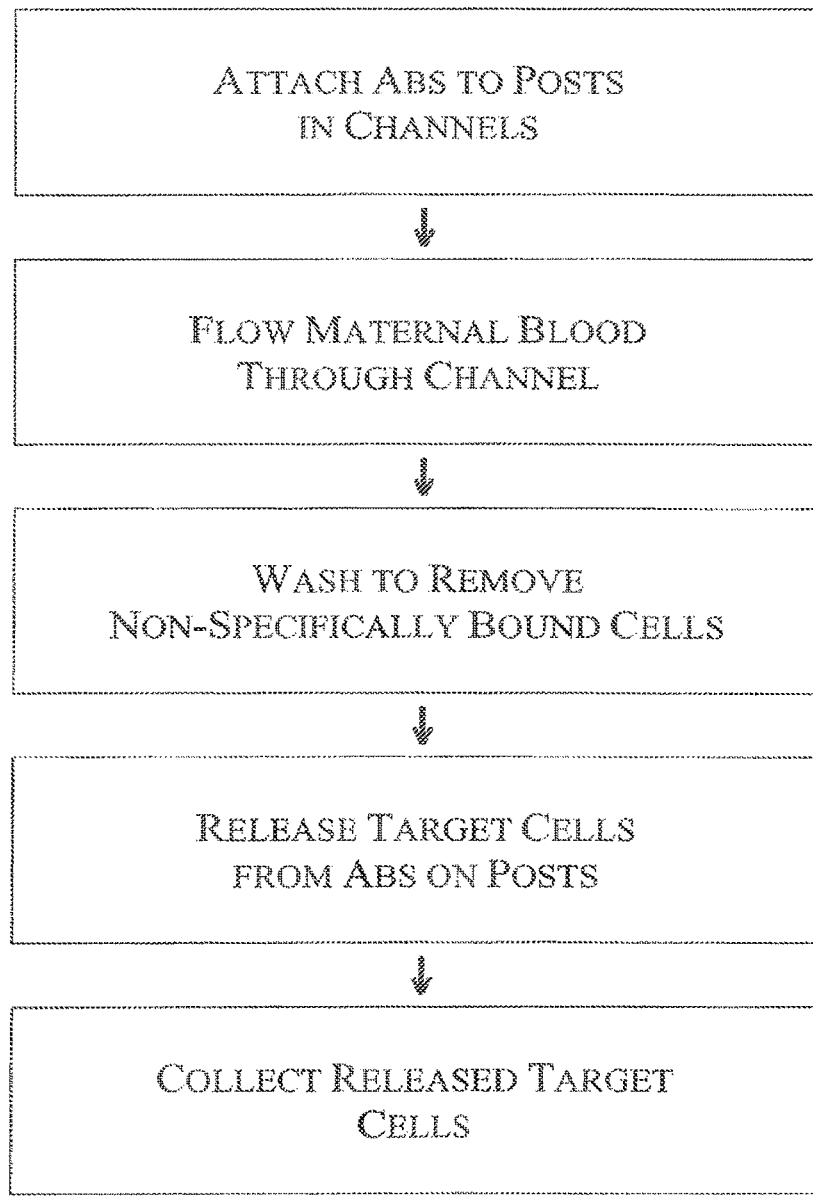
FIG. 11 is a flow sheet illustrating the steps of a cell recovery operation utilizing such a patterned post, cell separation device.

The following examples illustrate effective use of prototype microchannel devices of this type to sequester trophoblast cells from an extract of cervical mucus. The overall method is outlined in the flow sheet attached as FIG. 11. The examples should, of course, be understood to be merely illustrative of only certain embodiments of the invention and not to constitute limitations upon the scope of the invention which is defined by the claims which are appended at the end of this description.

EXAMPLE 1

A microflow device for separating biomolecules is constructed using a prototype substrate as generally illustrated in FIG. 1. The substrate is formed from PDMS and is bonded to a flat glass plate to close the flow channel. The interior surfaces throughout the collection region are derivatized by incubating for 30 minutes at room temperature with a 10 volume % solution of Dow Corning Z-6020. After washing with ethanol, they are treated with nonfat milk at room temperature for about one hour to produce a thin casein coating. Following washing with 10% ethanol in water, a treatment is effected to coat the interior with a permeable hydrogel formed from a prepolymer of isocyanate-capped PEG triols, average MW of 6000, using 1 part by weight prepolymer to 6 parts of organic solvent, i.e. acetonitrile and DMF, and mixing it with water and flowing it through the channel as described with respect to FIG. 9.

For this test, it is desired to isolate trophoblasts from a sample of cervical mucus, and antibodies to Trop-1 and Trop-2 are selected which are specific to ligands carried by the exterior surfaces of trophoblasts which are of fetal origin. Antibody (0.1 mg) was dissolved in 100 µl of 0.2M sodium borate/0.15 M NaCl containing 5 mM EDTA (pH 8.3) and reacted with 5 µl of 40 mM Traut's reagent at RT for one hour to effect thiolation. Excess Traut's reagent is reacted with 10 µl of 100 mM glycine followed by purification of the thiolated antibody on the Centricon-30™ membrane. Thiolation was confirmed by standard laboratory procedures.

About 5 micrograms total of the thiolated anti-Trop-1 and 2 in aqueous solution, at a concentration of about 0.5 mg/ml, are supplied to the pretreated microflow device, and the solution is left to incubate for 2 hours at 25° C. Following this incubation period, the flow channel is flushed with a 1% PBS/BSA to give antibody-coated surfaces which were then used to try to isolate fetal trophoblast cells.

Cervical mucus from expectant mothers (8-12 weeks gestation) was diluted to 10 ml with HAM's media (InVitrogen) and treated with DNAse (120 units) at 37° C. for 30 minutes. After filtering through a 100 µm cell strainer, the cells were spun at 1500 RPM for 30 minutes. The cell pellet was resuspended in HAM's media (100 µl) and passed through the Trop-1 and Trop-2 coated microchannel by hooking the microflow separation device up to outlet tubing from a Harvard Apparatus syringe pump which is filled with about 50 microliters of this cell suspension of cervical mucus extract. The syringe pump is operated to produce a slow continuous flow of the sample liquid through the microflow device at room temperature and a rate of about 10 µl/min. During this period, the Trop-1 and Trop-2 Abs, that have been attached to the surfaces in the collection region where the random pattern of transverse posts is located, capture trophoblasts that are present in the sample. After the entire sample has been delivered by the syringe pump, a slow flushing is carried out with a 1% PBS/BSA aqueous buffer. About 100 µl of this aqueous buffer is fed through the device over a period of about 10 minutes, which effectively removes all non-specifically bound bio material from the flow channel in the device. Two additional washings are then carried out, each with about 100 µl of 1% PBS plus 1% BSA over a period of about 10 minutes.

At this time, inasmuch as the device is made of optically clear material, microscopic examination can be made of the effects of the capture, as by using photomicroscopy. The bound cells were stained with cytokeratin 7 and cytokeratin 17 that are specific to captured cells which are of trophoblast origin. By counting Cells in such photomicrographs, it is estimated that substantially 97% of the trophoblasts estimated to be present in the sample have been captured in the patterned post collection region, which is considered to be a very excellent result.

In a repeat of this procedure through the capture and washing steps, instead of staining in situ, the captured trophoblasts are released by causing a solution of 100 µl of a 0.25% solution of trypsin to slowly flow through the flow channel at 27° C. over a period of 20 minutes. This reagent causes digestion of the Abs, releasing the trophoblasts into the aqueous flow where they pass through the outlet and are collected. Analysis of the collected cells by PCR. and FISH based technologies shows that they are indeed the trophoblasts that were targeted by the Abs that were employed.

EXAMPLE 2

Another microflow device for separating biomolecules is constructed using a prototype substrate as described in Example 1. The interior surfaces of the substrate are derivatized, washed with ethanol, and treated with nonfat milk as in Example 1. Following washing with 10% ethanol in water, a treatment is effected using the prepolymer, BSA, and antibodies Trop-1 and Trop-2 in borate buffer. 1 mg/ml antibody aqueous solution in 100 mM sodium borate pH 8.0 containing BSA is used. The specific formulation comprises 100 mg of the same prepolymer in Acn/DMF; 350 µl of 0.25 mg/ml antibody mix in borate buffer; and 350 µl of 1 mg/ml BSA in borate buffer, and it contains about 2% polymer by weight.

The antibodies are not thiolated, and about 5 microliters total of the Trop-1 and 2 aqueous hydrogel solution are supplied to the pretreated microflow device. The solution is left to incubate for about 30 minutes at 25° C., and following this incubation period, the flow channel is flushed with mineral oil which is slowly pushed into the flow channel to displace and push out excess hydrogel. This results with an oil-filled flow channel which has a thin layer of hydrogel coating separating the oil from the PDMS material. After 3 hours, the hydrogel has fully cured, and oil is flushed out with a 1× PBS/0.1% Tween solution. The device is then filled with 1× PBS solution to preserve the Abs.

Cervical mucus from expectant mothers is diluted, treated, filtered, centrifuged and resuspended in 100 µl of HAM' s media. The liquid cell suspension sample is passed through the Trop-1 and Trop-2 coated microchannel using a Harvard Apparatus syringe pump, as in Example 1. After the entire sample is delivered by the syringe pump, a slow flushing is carried out with a 1% PBS/BSA aqueous buffer. About 100 µl of this aqueous buffer is fed through the device over a period of about 10 minutes to effectively remove all non-specifically bound biomaterial from the flow channel in the device. Two additional washings are then carried out, each with about 100 µl of 1% PBS plus 1% BSA over a period of about 10 minutes.

Microscopic examination is again made of the effects of the capture by using photomicroscopy, after staining the bound cells with cytokeratin 7 and cytokeratin 17. By counting cells in such photomicrographs, it is determined that excellent capture of the trophoblasts estimated to be present in the sample is achieved.

EXAMPLE 3

Another microflow device for separating biomolecules is constructed using a prototype substrate as described in Example 1. The interior surfaces of the substrate are derivatized, washed with ethanol, and treated with nonfat milk as in Example 1.

Following washing with 10% ethanol in water, a treatment is effected using 10 µl of 2.5 mM NHS-polyglycine (ave. MW about 4500) in 0.2 MOPS/0.5 M NaCl, pH 7.0, by incubating at RT for 2 hours with gentle pumping of the solution back and forth in the channel to provide agitation. The microchannel is washed three times with 500 µl of pH 7.0 MOPS buffer to obtain maleimido-polyGly-coated channels.

Antibodies Trop-1 and Trop-2, which are specific to ligands carried by the exterior surfaces of trophoblasts are treated as in Example 1 to thiolate them.

About 5 micrograms total of thiolated anti-Trop-1 and 2 in aqueous solution, at a concentration of about 0.25 mg/ml, are supplied to the pretreated microflow device, and the solution is left to incubate for 2 hours at 25° C. Following this incubation period, the flow channel is flushed (3 times) with a 1% PBS/BSA to provide the antibody-coated surfaces which are then used to try to isolate fetal trophoblast cells.

Cervical mucus from expectant mothers is diluted, treated, filtered, centrifuged and resuspended in 100 µl of HAM's media. The liquid cell suspension sample is passed through the Trop-1 and Trop-2 coated microchannel using a Harvard Apparatus syringe pump. After the entire sample is delivered by the syringe pump, a slow flushing is carried out with a 1% PBS/BSA aqueous buffer. About 100 µl of this aqueous buffer is fed through the device over a period of about 10 minutes to effectively remove all non-specifically bound biomaterial from the flow channel in the device. Two additional washings are then carried out, each with about 100 µl of 1% PBS plus 1% BSA over a period of about 10 minutes.

Microscopic examination is again made of the effects of the capture by using photomicroscopy after staining the bound cells with cytokeratin 7 and cytokeratin 17. By counting cells in such photomicrographs, it is determined that good capture of the trophoblasts estimated to be present in the sample is achieved.

EXAMPLE 4

A plurality of microflow devices, similar to that employed in Example 1 and as shown in FIG. 3, are formed to test the improvement that results from operation at 45° as opposed to horizontal. The improved effectiveness of such an angularly disposed microflow device 71 is tested by employing a feed liquid that employs a mixture of BeWo and Jurkat cells. BeWo cells are chosen because they express Trop-1 and Trop-2 antigens, whereas Jurkat cells express neither and thus serve as negative control cells, The interior surface of the microflow device 71 is pretreated and then coated with a permeable hydrogel as described in Example 2 using Anti-Trop-1 and Anti-Trop-2 in aqueous solution in the coating formulation. The interior of the microflow device is filled with the Ab coating solution and allowed to incubate for about 30 minutes at 25° C. Flushing is carried out using mineral oil and then PBS buffer as in Example 2.

Sufficient test feed solution is prepared for six test runs; it contains about 3,000 BeWo cells and about 3,000 Jurkat cells in a 1% BSA/PBS buffer. The feed solution is split into six aliquots, with each of the aliquots containing about 500 BeWo cells and about 500 Jurkat cells. Three of the identical microflow devices 71 are arranged horizontally, and one aliquot of the mixed cell feed liquid is caused to flow through each as a result of suction supplied by a vacuum pump. Three different rates of flow are used for the three test devices: flow rates of 1 µl/min, of 5 µl/min and of 10 µl/min.

Following flow through these three test devices, washing was carried out with a PBS buffer, and each individual device was then examined by microscopy. Each of the two groups of captured cells was separately counted manually by microscopy. With respect to the targeted BeWo cells, it was found that, at the lowest flow rate, about 47% of the BeWo cells were captured in the inlet region and only about 32% in the collection channel, with the remainder residing in the outlet region. At the flow rate of 5 μl/min, the percentage of BeWo cells captured in the collection channel region dropped slightly to about 27%, and although more cells were still captured in the inlet region, the largest percentage of cells collected in the outlet region. At the highest flow rate through the device in the horizontal orientation, only 10% of the BeWo cells are captured in the collection channel region, whereas about 65% of the cells collect in the outlet region. With respect to the Jurkat cells, at the lowest flow rate, about 20-25% of the cells were captured in each of the inlet and channel regions, and at the middle flow rate, only about 10% of the Jurkat cells were captured in the collection channel region. As expected, the amount of these cells which collect in the outlet region increases with each increase in flow rate, where all the cells that are not retained in the device collect as a mixture.

The experiment is then run using three more, identical, microflow devices, with each oriented at 45° from the vertical. This time, flow rates of 1, 3 and 5 μl/min are used. The improvement in the desired cell capture of BeWo cells in the collection channel region is striking At the lowest flow rate, about 75% of the BeWo cells are now captured in the collection channel region. This value rises to about 82% at the middle flow rate of 3 μl/min, and remains at about 60% at the highest flow rate tested of 5 μl/min. On the other hand, although the nonspecific binding of the Jurkat cells in the collection region is relatively high at the lowest flow rate, i.e. about 45%, it drops to only about 15% at 3 μl/min, and less than 5% at the highest flow rate. Accordingly, the improvement in performance at the 45° orientation versus horizontal is very substantial when operating at flow rates of about 3-5 μl/min, collecting over 80% of the cells rather than only about 27%. Calculations show that, by operating at a flow rate which is equal to a velocity through the collection chamber region of about 0.27 mm/sec, excellent collection of the targeted cells, with minimum contamination by nonspecifically bound cells, is obtained.

Although the invention has been described with regard to certain preferred embodiments which constitute the best mode presently known to the inventor for carrying out this invention, it should be understood that various changes and modifications as would be obvious to one having ordinary skill in this art may be made without departing from the scope of the invention which is defined in the claims which follow. For example, although certain preferred materials have been described for the fabrication of the substrate in which the microchannels are defined, there is a broad range of structural materials that may be employed as are well known in this art as being suitable for laboratory devices such as this. Although the emphasis has generally been upon the separation of fetal cells from a maternal blood sample or trophoblasts from a cervical mucus extract, it should be understood that the invention is useful for separating a wide variety of blood cells, e.g. nucleated erythrocytes, lymphocytes and the like, metastatic cancer cells, stem cells, etc.; moreover, other biological materials, e.g. proteins, carbohydrates, viruses, etc., might also be separated from a liquid sample, When the sample contains specific subpopulations of cells, the target cells to be captured may be a group of unwanted cells to be separated from rare cells or the like. Moreover, once targeted cells have been collected, they may also be lysed in situ to provide the cell DNA, which may be collected for analysis downstream or alternatively subjected to PCR within the collection chamber. U.S. Published Application 2003/0153028 teaches lysing such bound cells to obtain the nucleic acid that is released. If there are two different subpopulations of target cells in a sample, different sequestering agents may be attached to the posts in a pair of upstream and downstream collection chambers. In another situation, one genus of cells may be first collected in an upstream collection chamber, released, and then screened again in a downstream chamber to isolate a subgenus of cells.

The invention claimed is:

1. A microflow apparatus comprising:
    a body comprising an inlet passageway, an outlet, and a microchannel arrangement extending between said inlet passageway and outlet to form a collection region,
    wherein said microchannel arrangement comprises a plurality of transverse separator posts being integral with a base surface and projecting therefrom,
    wherein said posts are arranged in an irregular pattern that has the characteristics selected from the group consisting of
    1) said posts having at least two different cross-sectional sizes, about 70 μm to about 130 μm in diameter,
    2) said posts having at least two different cross-sectional sizes and minimum separation spacing between posts is from about 50 μm to about 70 μm,
    3) said posts having at least two different cross-sectional sizes and occupying about 15% to about 25% of the total volume of the collection region,
    4) said posts having about 70 μm to about 130 μm in diameter and minimum separation spacing between posts is from about 50 μm to about 70 μm,
    5) said posts having about 70 μm to about 130 μm in diameter and occupying about 15% to about 25% of the total volume of the collection region, and
    6) said posts having minimum separation spacing between posts from about 50 μm to about 70 μm and occupying about 15% to about 25% of the total volume of the collection region.

2. The apparatus of claim 1, wherein said posts are aligned substantially perpendicular to said base surface.

3. The apparatus of claim 1, wherein said posts are arranged in the irregular pattern across the entire width of said collection region.

4. The apparatus of claim 1, wherein the surface of said microchannel arrangement is coated with a sequestering agent.

5. The apparatus of claim 1, wherein the surface of said microchannel arrangement is coated with a sequestering agent and wherein the sequester agent is coupled to the surface of the microchannel arrangement by a linker.

6. The apparatus of claim 1, wherein the said microchannel arrangement is sealed with a plate.

7. The apparatus of claim 6, wherein the said posts are affixed to said plate at their distal ends.

8. The apparatus of claim 6, wherein said plate is optically transparent.

9. The apparatus of claim 1, wherein the base surface is optically transparent.

10. The apparatus of claim 1, wherein said outlet comprises an outlet passageway and wherein said inlet passage way and said outlet passageway are angularly aligned at 90 degrees to each other.

11. The apparatus of claim 1, wherein the surface of said microchannel arrangement is coated with a hydrophilic layer.

12. A method of capturing a target cell in a sample comprising causing a body of liquid containing said sample to flow through said microchannel arrangement of the apparatus of claim 1, wherein the surface of said microchannel arrangement is coated with a sequestering agent capable of capturing the target cell in the sample.

13. The method of claim 12, wherein the target cell is a cancer or tumor cell.

14. The method of claim 12, wherein the target cell is a fetal cell.

15. The method of claim 12, wherein the body of liquid containing said sample flows through said microchannel arrangement at a speed of about 0.5 mm to about 5 mm per second.

16. The method of claim 12, wherein the body of liquid containing said sample flows through said microchannel arrangement at a speed of about 0.5 µL to about 10 µL per minute.

17. The microflow apparatus of claim 1, wherein said posts are arranged in an irregular pattern that has the characteristics selected from the group consisting of
1) said posts having at least two different cross-sectional sizes and minimum separation spacing between posts is from about 50 µm to about 70 µm,
2) said posts having at least two different cross-sectional sizes and occupying about 15% to about 25% of the total volume of the collection region,
3) said posts having about 70 µm to about 130 µm in diameter and minimum separation spacing between posts is from about 50 µm to about 70 µm,
4) said posts having about 70 µm to about 130 µm in diameter and occupying about 15% to about 25% of the total volume of the collection region, and
5) said posts having minimum separation spacing between posts from about 50 µm to about 70 µm and occupying about 15% to about 25% of the total volume of the collection region.

* * * * *